US011185522B2

(12) United States Patent
Tejedor Jorge et al.

(10) Patent No.: US 11,185,522 B2
(45) Date of Patent: Nov. 30, 2021

(54) CILASTATIN FOR USE IN THE TREATMENT OF SEPSIS

(71) Applicant: FUNDACIÓN PARA LA INVESTIGACIÓN BIOMÉDICA DEL HOSPITAL GREGORIO MARAÑÓN, Madrid (ES)

(72) Inventors: Alberto Tejedor Jorge, Madrid (ES); Alberto Lazaro Fernandez, Madrid (ES); Blanca Humanes Sanchez, Madrid (ES); Maria Angeles Gonzalez-Nicolas Gonzalez, Madrid (ES)

(73) Assignee: FUNDACIÓN PARA LA INVESTIGACIÓN BIOMÉDICA DEL HOSPITAL GREGORIO MARAÑÓN, Madrid (ES)

( * ) Notice: Subject to any disclaimer, the term of this patent is extended or adjusted under 35 U.S.C. 154(b) by 0 days.

(21) Appl. No.: 16/312,825

(22) PCT Filed: Jun. 23, 2017

(86) PCT No.: PCT/EP2017/065609
§ 371 (c)(1),
(2) Date: Dec. 21, 2018

(87) PCT Pub. No.: WO2017/220810
PCT Pub. Date: Dec. 28, 2017

(65) Prior Publication Data
US 2020/0069623 A1 Mar. 5, 2020

(30) Foreign Application Priority Data

Jun. 24, 2016 (EP) .................... 16382299

(51) Int. Cl.
| | | |
|---|---|---|
| *A61K 31/198* | (2006.01) | |
| *A61P 13/12* | (2006.01) | |
| *A61K 9/00* | (2006.01) | |
| *A61K 45/06* | (2006.01) | |

(52) U.S. Cl.
CPC .......... *A61K 31/198* (2013.01); *A61K 9/0019* (2013.01); *A61K 9/0029* (2013.01); *A61K 45/06* (2013.01); *A61P 13/12* (2018.01)

(58) Field of Classification Search
CPC .......... A61K 31/198; A61P 13/12; A61P 31/04
See application file for complete search history.

(56) References Cited

U.S. PATENT DOCUMENTS

| | | | |
|---|---|---|---|
| 9,216,185 B2 * | 12/2015 | Tejedor Jorge | A61P 39/00 |
| 9,522,128 B2 * | 12/2016 | Tejedor Jorge | A61K 31/167 |
| 9,757,349 B2 * | 9/2017 | Tejedor Jorge | A61K 45/06 |
| 2011/0165264 A1 | 7/2011 | Tejedor Jorge et al. | |

FOREIGN PATENT DOCUMENTS

| | | |
|---|---|---|
| CN | 1878564 A | 12/2006 |
| WO | 2017/025802 A1 | 2/2017 |

OTHER PUBLICATIONS

Camano et al., "Cilastatin Attenuates Cisplatin-Induced Proximal Tubular Cell Damage," *The Journal of Pharmacology and Experimental Therapeutics* 334(2):419-429, 2010.
Del Valle et al., "Efficacy and Safety of Imipenem/Cilastatin in the Empirical Treatment of Septicemia," *Scand J Infect Dis Suppl.* 52:20-25, 1987.
Humanes et al., "Cilastatin protects against cisplatin-induced nephrotoxicity without compromising its anticancer efficiency in rats," *Kidney International* 82:652-663, 2012.
Humanes et al., "Protective Effects of Cilastatin against Vancomycin-Induced Nephrotoxicity," *Biomed Research International*, 12 pages, 2015.
Kabbara et al., "Evaluation of the appropriateness of imipenem/cilastatin prescription and dosing in atertiary care hospital," *Infection and Drug Resistance* 8:31-38, 2015.
Kuo et al., "Meropenem versus imipenem/cilastatin in the treatment of sepsis in Chinese patients," *Zhonghua YiXue Za Zhi* (Taipei) 63(5):361-367, 2000 (abstract only).
Lazaro et al., "Novel Strategies in Drug-Induced Acute Kidney Injury," *InTech*, pp. 381-396, 2012.
Moreno-Gordaliza et al., "Elemental Bioimaging in Kidney by LA-ICP-MS As a Tool to Study Nephrotoxicity and Renal Protective Strategies in Cisplatin Therapies," *Anal. Chem.* 83:1933-7940, 2011.
Nagano et al., "Therapeutic Efficacy of BO-3482, a Novel Dithiocarbamate Carbapenem, in Mice Infected with Methicillin-Resistant *Staphylococcus aureus*," *Antimicrobial Agents and Chemotherapy* 47(10):2278-2281, 1997.
Perez et al., "Inhibition of brush border dipeptidase with cilastatin reduces toxic accumulation of cyclosporin A in kidney proximal tubule epithelial cells," *Nephrology Dialysis Transplantation* 19:2445-2455, 2004.
Romanovsky et al., "Pathophysiology and management of septic acute kidney injury," *Pediatric Nephrology* 29:1-12, 2014.
Zarjou et al., "Sepsis and Acute Kidney Injury," *J Am Soc Nephrol* 22:999-1006, 2011.
Merck Sharp & Dohme Limited, "Primaxin IV 500 mg/500 mg powder for solution for infusion," retrieved from https://www.medicines.org.uk/emc/product/1515/smpc/print on Sep. 10, 2020 (11 Pages).
Robbins et al., U.S. Appl. No. 62/203,704, filed Aug. 11, 2015, 53 pages.
Robbins et al., U.S. Appl. No. 62/264,032, filed Dec. 7, 2015, 62 pages.

(Continued)

*Primary Examiner* — James D. Anderson
(74) *Attorney, Agent, or Firm* — Seed IP Law Group LLP

(57) ABSTRACT

The present invention relates to the treatment of sepsis and sepsis-associated acute kidney injury (SA-AKI). More specifically, it relates to cilastatin for use in a method of treating sepsis and/or SA-AKI and reducing its associated mortality, in a mammalian subject. It is further directed to methods for treating sepsis and/or SA-AKI; and to pharmaceutical compositions for use in the methods of the invention.

23 Claims, 13 Drawing Sheets

(56) References Cited

OTHER PUBLICATIONS

Shen et al., "Pharmaceutical Care for a Patient with Sepsis Complicating with Acute Renal Failure Treated by Vancomycin," *China Pharmacy* 23(30):2790-2792, 2012 (With English Translation) (9 Pages).

\* cited by examiner

FIG. 8Cont.
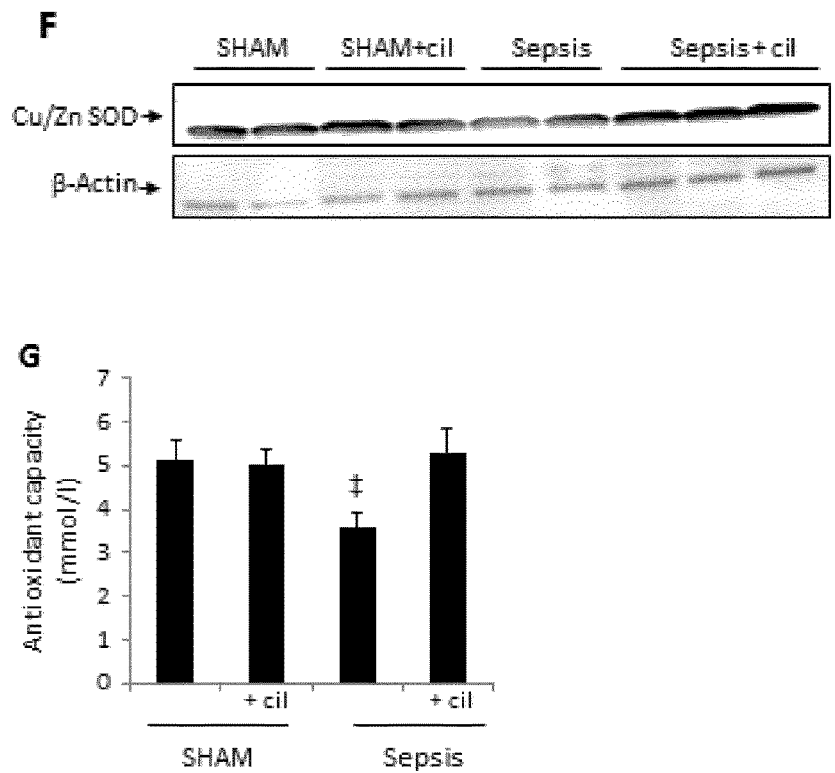

CILASTATIN FOR USE IN THE TREATMENT OF SEPSIS

FIELD OF INVENTION

The present invention relates to the medical and pharmaceutical field, in particular to the field of research and development of new drugs for the treatment of sepsis and sepsis-associated acute kidney injury (SA-AKI). More specifically, it relates to cilastatin for use in a method of treating sepsis and/or SA-AKI and reducing its associated mortality, in a mammalian subject. It is further directed to methods for treating sepsis and/or SA-AKI; and to pharmaceutical compositions for use in the methods of the invention.

BACKGROUND OF THE INVENTION

Sepsis is a deleterious systemic inflammatory response to infection. There is a continuum of severity ranging from sepsis to severe sepsis (acute organ dysfunction secondary to documented or suspected infection) and septic shock (severe sepsis plus hypotension not reversed with fluid resuscitation). It is a major cause of morbidity and mortality worldwide (Angus D C et al, N Engl J Med. 2013; 369(21): 2063, Jawad I et al, J. Glob. Health, 2012; 2(1), 10404, Fleischmann C et al, Am J Respir Crit Care Med. 2016; 193(3): 259-72). In the United States sepsis is the tenth leading cause of death with approximately 250.000 annual deaths contributing to significant economic costs (Angus D C et al, Crit Care Med. 2001; 29(7):1303-10).

Prompt recognition of the septic patient is critical, and early localization along the sepsis spectrum of illness (i.e., sepsis, severe sepsis, septic shock) helps to define the early goals of management. The first priority in any patient with severe sepsis or septic shock is stabilization of respiration. Next, perfusion to the peripheral tissues should be restored and antibiotics administered (Surviving Sepsis Campaign Guidelines 2012: http://www.sccm.org/Documents/SSC-Guidelines.pdf).

In the setting of severe sepsis and/or septic shock, it has been demonstrated that delayed antibiotic administration is clearly associated with increased mortality. Accordingly, the international guidelines for management of severe sepsis and septic shock establish the administration of effective intravenous antimicrobials within the first hour of recognition as a goal for the therapy, and further recommend the initial empiric anti-infective therapy of one or more drugs that have activity against all likely pathogens (bacterial and/or fungal and/or viral) and that penetrate in adequate concentrations into tissues presumed to be the source of sepsis (Surviving Sepsis Campaign Guidelines 2012, Tupchong et al. African Journal of Emergency Medicine 2015, 5, 127-135).

The current treatment for sepsis with an emphasis on antibiotics and eradicating the source of infection, supporting blood pressure, organ blood flow, and ventilation has shown not to be very effective in reducing mortality associated to sepsis which as above-mentioned is still very high. Therefore, there is an urgent need to develop innovative and efficacious therapies for the treatment of sepsis.

The sepsis response typically begins with a microbial infection. The recognition of microbial components such as lipopolysaccharide (LPS), peptidoglycan, lipoteichoic acid, and unmethylated CpG DNA by toll like receptors (TLRs) (Takeuchi and Akira, 2001) leads to the rapid activation of the innate immune response and the release of a variety of humoral mediators, including glucocorticoids, catecholamines, and proximal pro-inflammatory cytokines like tumor necrosis factor a (TNF-α), interleukin-1 (IL-1), and IL-6. This pro-inflammatory state has been defined as being a systemic inflammatory response syndrome (SIRS).

Exaggerated production of pro-inflammatory cytokines and the induction of more distal mediators such as nitric oxide, platelet activation factor, and prostaglandins have been implicated in the endothelial changes and induction of a pro-coagulant state that leads to hypotension, inadequate organ perfusion, and necrotic cell death associated with multiple organ dysfunction syndrome (MODS). However, most patients survive this initial SIRS event and the pro-inflammatory state ultimately resolves. After that, the patient frequently enters an immunological state that has been recently termed a compensatory anti-inflammatory response syndrome (CARS) (see FIG. 1 and Oberholzer et al. 2001; FASEB J. 15(6):879-92).

Multiple-organ dysfunction syndrome (MODS) has been identified as one of the most fatal complications of sepsis. Many agents targeting a variety of steps in the systemic inflammatory response have been developed over the years, but most of these have shown little or no effectiveness in clinical trials (Zarjou et al., 2011, J Am Soc Nephrol 22: 999-1006; Swaminathan S., et al. Seminars in nephrology 2015, 35(1):38-54).

Indeed, only one therapeutic agent, activated drotrecogin alfa, also known as recombinant human activated protein C, has been shown to improve survival in patients with severe sepsis and septic shock (Zarjou et al., 2011, J Am Soc Nephrol 22: 999-1006). Xigris™, containing as active ingredient activated drotrecogin alfa, was authorised in the European Union under exceptional circumstances in 2002 for the treatment of severe sepsis in adult patients with multiple organ failure, in addition to best standard care. On Oct. 25, 2011, Eli Lilly & Co. withdrew Xigris from the market after a major study showed no efficacy for the treatment of sepsis (http://www.ema.europa.eu/docs/en_GB/document_library/Press_release/2011/10/WC50 0116970.pdf).

In this context of multiple organ failure, acute kidney injury (AKI) has been reported as a particularly serious complication in patients with severe sepsis, where it is the leading cause of death among critically ill patients (Emlet D R et al, Semin Nephrol. 2015; 35(1):85-95, Zarbock A et al, Curr Opin Crit Care. 2014; 20(6): 588-95, Schrier R W et al, N Engl J Med. 2004; 351(2):159-69) with a high mortality rate of 50% to 80%. It has been described that the mortality of septic patients with AKI is about 75%, while those with severe sepsis without AKI ranges between 27 and 32% (Hoste E A et al, Crit Care. 2006; 10(3):R73).

Septic AKI (SA-AKI) has been described as being distinct from AKI without sepsis. Notably, it has been reported that SA-AKI is driven by a number of characteristic pathophysiological mechanisms, carrying a unique profile of timing (onset, duration), and being associated with different short- and long-term outcomes in comparison with non-septic AKI (Alobaidi et al., Seminars in nephrology 2015, 35(1), 2-11; Zarjou et al., 2011, J Am Soc Nephrol 22: 999-1006). The pathophysiology of AKI in sepsis is complex and multifactorial. It includes intrarenal hemodynamic changes, endothelial dysfunction, infiltration of inflammatory cells in the renal parenchyma, intraglomerular thrombosis, and obstruction of tubules with necrotic cells and debris, see FIG. 1 (Zarjou et al., 2011, J Am Soc Nephrol 22: 999-1006; Wan et al., Crit Care Med 2008, 36:S198-S203).

Moreover, it has been described that SA-AKI is associated with a more acute progression and severity of the illness and a worse prognosis and increased mortality when compared to non-septic AKI (Alobaidi et al., Seminars in nephrology 2015, 35(1), 2-11; and Godin et al., Seminars in nephrology 2015, 35(1), 12-22; Bagshaw et al. Crit. Care 2008, 12:R47; White et al. J Trauma Acute Care Surg. 2013, 75: 432-8).

Godin et al. (Seminars in nephrology 2015, 35(1), 12-22) particularly point to the fact that in septic patients renal recovery is highly unlikely when sepsis is not controlled because the mechanisms of insult persist. Even though, once sepsis is resolved, in clinical practice, the kidney is often one of the last organs to recover in patients with multiple organ failure caused by sepsis, the likelihood of renal recovery depending on a number of factors such as the patient's underlying characteristics, the severity of the underlying insult (e.g., hemodynamic changes, infection severity and multiple organ failure), and the iatrogenic insults associated with the process of care (e.g. nephrotoxic antibiotics and contrast media).

This is consistent with the fact that discouraging results have been obtained so far with nephroprotective drugs, such as diuretics, dopamine, inhibitors of angiotensin converting enzyme, inhibitors of caspases, etc. (Ronco et al., Clin J Am Soc Nephrol 2008, 3: 531-544). Several new therapeutic approaches for treating sepsis and septic AKI have been proposed including the targeting of early inflammation, late immune suppression, oxidative stress and molecular mechanisms of cell recovery (see for instance Swaminathan S., et al. Seminars in nephrology 2015, 35(1):38-54). Some of the new drugs with systemic anti-inflammatory effects have been reported to have a multiple organ protective effect (including liver, lung and/or kidney) and reduce mortality in animal sepsis models, such as for example CKD-712 (Park et al. Arch Pharm Res Vol 34, No 3, 485-494, 2011) and Kallistatin (Li et al., Critical Care 2015, 19:200).

Cilastatin was first described as a competitive inhibitor of dehydropeptidase I (DHP-I) which prevented hydrolysis of the peptide bond and opening of lactam rings. In the presence of cilastatin, dihydropeptidase I did not open the lactam ring of imipenem, prevented its absorption, and increased urinary excretion of imipenem, reducing its concentration in tubular cells (Clissold, Drugs 1987; 33(3):183-241, Birnbaum, Am J Med. 1985; 78(6A):3-21).

Thus, cilastatin has traditionally been used in combination with imipenem (a beta-lactam antibiotic) in order to protect it from DHP-I and prolong its antibacterial effect. However, cilastatin in and of itself does not have any antibacterial activity. For instance, it has been commercialized in Spain under the trade name Tienam® as a formulation for intravenous administration containing imipenem/cilastatin (1:1) in doses of 500 mg. Tienam® has been approved for the treatment of infections in adults and children of 1 year of age and above including complicated intra-abdominal infections; severe pneumonia including hospital and ventilator-associated pneumonia; intra- and post-partum infections; complicated urinary tract infections; and complicated skin and soft tissue infections. It further has been approved for the treatment of patients with bacterial septicemia that occurs in association with, or is suspected to be associated with any of said infections (http://www.aemps.gob.es/cima/pdfs/es/ft/57329/FT_57329.pdf). In the US, it has been marketed by Merck & Co., Inc under the trade name Primaxin®, e.g. pharmaceutical forms Primaxin I.V. 250 and Primaxin I.V. 500 which have been approved for bacterial septicemia (http://www.accessdata.fda.gov/drugsatfda_docs/label/2008/050587s065, 050630s0281b1.pdf). Finally, Del Valle J et al. (Scand J Infect Dis Suppl 1987, 52:20-5) and Kuo B I et al. (Zhonghua Yi Xue Za Zhi (Taipei) 2000, 63(5): 361-7) have also reported the use of imipenem/cilastatin in the treatment of sepsis. Cilastatin/imipenem has thus been previously used in the treatment of sepsis. It has not been used however in the treatment of septic AKI, indeed a dosage reduction of cilastatin/imipenem was recommended upon appearance of signs of renal failure. More recently, Kabbara W. K. et al. (Infection and Drug resistance 2015 (8), 31-38) published a study assessing whether the use of imipenem/cilastatin in a tertiary care hospital in Lebanon was in agreement with the existing guidelines and literature.

Moreover, Nagano et al. (Antimicrobial Agents and Chemotherapy 1997, 41(10), 2278-2281) reported the in vivo testing of cilastatin in combination with another carbapenem antibiotic, namely dithiocarbamate carbapenem (BO-3482) in the treatment of sepsis.

Cilastatin has subsequently been described as reducing renal damage of nephrotoxic drugs other than beta-lactams (WO 97/37649). More specifically, the inventors have reported the beneficial effects in vitro and in vivo of cilastatin against common nephrotoxic agents used in human clinical settings such as cisplatin, cyclosporine A or vancomycin without reducing their therapeutic activity (Humanes B et al, Kidney International. 2012; 82(6):652-663, Moreno-Gordaliza E et al, Analytical Chemistry. 2011; 83(20):7933-7940, Camano S et al. Journal of Pharmacology and Experimental Therapeutics. 2010; 334(2):419-429, Perez M et al, Nephrology Dialysis Transplantation. 2004; 19(10):2445-2455, Lazaro A et al, Pharmacology, edited by Gallelli L, chapter 18. Rijeka, Croatia: InTech; 2012. pp. 381-396, Humanes B et al, Biomed Res Int. 2015; 2015:704382, US2011/0165264). Indeed, in previous work, the inventors described that cilastatin is an inhibitor of DHP-I which is present in the cholesterol rafts of the brush border of renal proximal tubular epithelial cells (PTECs) (Camano S et al. Journal of Pharmacology and Experimental Therapeutics. 2010; 334(2):419-429) and reported that the binding of cilastatin to DHP-I in the brush border of PTECs produces an interruption of the free movement of the lipid rafts causing the reduction or cancellation of key steps of the extrinsic pathway of apoptosis, with a protective effect against oxidative stress and cell death by apoptosis induced by nephrotoxic agents (Humanes B et al, Kidney International. 2012; 82(6):652-663, Camano S et al. Journal of Pharmacology and Experimental Therapeutics. 2010; 334 (2):419-429, Humanes B et al, Biomed Res Int. 2015; 2015:704382).

SUMMARY OF THE INVENTION

Protective effects of cilastatin against drug-induced nephrotoxicity have previously been described to be obtained through binding to DHP-I located in the brush border of renal proximal tubule epithelial cells (RPTECs) of the kidney. DHP-I has not been reported to be expressed in any other of those organs typically involved in the multiple organ failure characterising severe sepsis and septic shock, such as lung, heart or liver (http://www.proteinatlas.org/ENSG00000015413-DPEP1/tissue).

Contrary to the well stablished assumption that it is very difficult to obtain renal recovery in the complex physiopathological setting of sepsis without first resolving the underlying mechanisms of renal insult such as a prolonged hypotension, the microbial infection, and the existing multiple organ failure, it has now been surprisingly found by the inventors that cilastatin is successfully treating SA-AKI and reducing sepsis-associated mortality.

In this sense, the inventors have demonstrated that treatment with cilastatin as single agent has markedly protective effects against polymicrobial infection caused by cecal ligation puncture model (CLP)-induced sepsis preventing lethality and ameliorating sepsis-induced kidney injury in rats. This is evidenced by a 30% reduction in mortality (FIG. 13). The obtained experimental data also showed an improvement in renal function parameters such as creatinine or blood urea nitrogen levels (BUN) previously elevated by sepsis (FIG. 2), partially restoring the levels of KIM-1, a novel early biomarker of AKI (FIG. 3), as well as a reducing damage in renal tissue (FIG. 4). Moreover, cilastatin has shown to reduce kidney apoptosis occurring in SA-AKI (FIGS. 5-7), to increase kidney cells antioxidant capacity (FIG. 8) and reduce lipid peroxidation (FIG. 9). In addition, cilastatin has shown effects in treating sepsis induced inflammation. In particular, it decreases monocytes/macrophages recruitment and infiltration into the kidney (FIG. 10) and reduces the expression of VCAM-1 and ICAM-1 molecules mediating the adhesion of leukocytes to the vascular endothelium (FIG. 11). Cilastatin has further shown to significantly decrease the levels of profibrotic TGFβ cytokine in septic animals (FIG. 12).

These findings support the use of cilastatin as a preventive or therapeutic agent in the treatment of sepsis and sepsis-induced renal injury. It is particularly relevant to note that a significant reduction in mortality of the sepsis-induced animal model was obtained with the administration of cilastatin as single therapy, i.e., without the co-administration of an antimicrobial therapy to treat the underlying infection. Therefore, cilastatin has been identified by the inventors as a new therapeutic strategy for treating septic patients.

The first aspect of the invention relates to cilastatin for use in a preventive or therapeutic method of treating sepsis in a mammalian subject, with the proviso that when cilastatin is administered in combination with another drug said other drug is not imipenem (i.e. cilastatin is not administered in combination with imipenem).

In addition, the present invention provides a method of treating sepsis comprising administering to a subject in need of such treatment a prophylactic or therapeutically effective amount of cilastatin, with the proviso that when cilastatin is administered in combination with another drug said other drug is not imipenem (i.e. cilastatin is not administered in combination with imipenem).

It further provides the use of cilastatin in the manufacture of a medicament for the preventive or therapeutic treatment of sepsis, with the proviso that when cilastatin is administered in combination with another drug said other drug is not imipenem (i.e. cilastatin is not administered in combination with imipenem).

In a particular embodiment of any of the above, when cilastatin is administered in combination with another drug, said other drug is not a beta-lactam antibiotic.

In a second aspect, the invention relates to cilastatin for use in a preventive or therapeutic method of treating sepsis-associated acute kidney injury (SA-AKI) in a mammalian subject.

In addition, the present invention provides a method of treating SA-AKI comprising administering to a subject in need of such treatment a prophylactic or therapeutically effective amount of cilastatin.

It further provides the use of cilastatin in the manufacture of a medicament for the preventive or therapeutic treatment of SA-AKI.

In a third aspect, the invention refers to cilastatin for use in a method of treatment for reducing mortality in a mammalian subject which suffers or is at risk of suffering from sepsis, preferably which suffers from sepsis and suffers or is at risk of suffering from SA-AKI.

In addition, the present invention provides a method for reducing mortality in a mammalian subject which suffers or is at risk of suffering from sepsis, preferably which suffers from sepsis and suffers or is at risk of suffering from SA-AKI, comprising administering to a subject in need of such treatment a prophylactic or therapeutically effective amount of cilastatin.

It further provides the use of cilastatin in the manufacture of a medicament for reducing mortality in a mammalian subject which suffers or is at risk of suffering from sepsis, preferably which suffers from sepsis and suffers or is at risk of suffering from SA-AKI.

In a particular embodiment of any of the above, when cilastatin is administered in combination with another drug, said other drug is not a beta-lactam antibiotic.

In a further aspect, the invention relates to a pharmaceutical composition comprising cilastatin for use in a method of treatment according to any of the above aspects, and further comprising a pharmaceutically acceptable carrier, additive and/or excipient. In a particular embodiment, when cilastatin is administered in combination with another drug, said other drug is not a beta-lactam antibiotic.

Data are expressed as mean±s.e.m., n=8-10 animals per group. *P≤0.005; †≤0.01; ‡≤0.05 vs. all other groups. Cil, cilastatin; a.u., arbitrary units.

Figure 7:
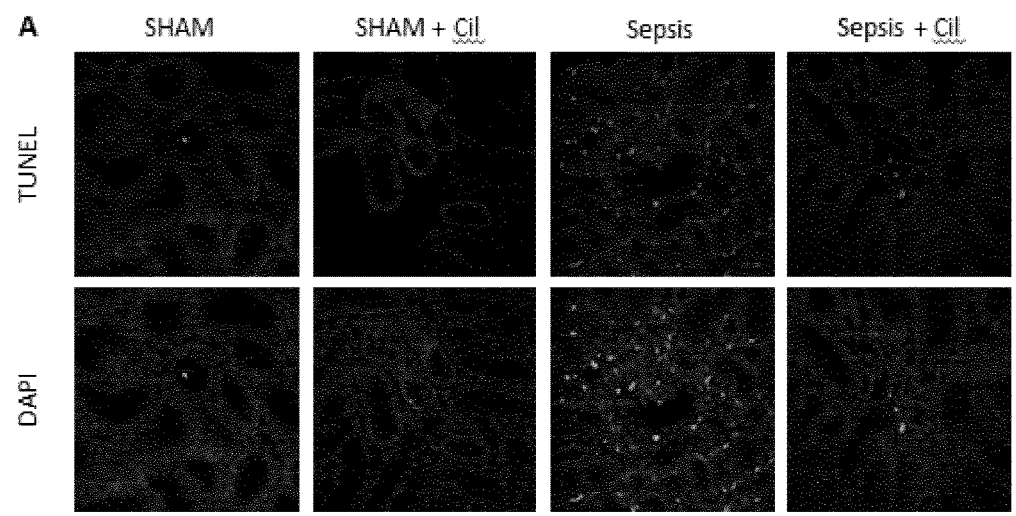
Figure 7:
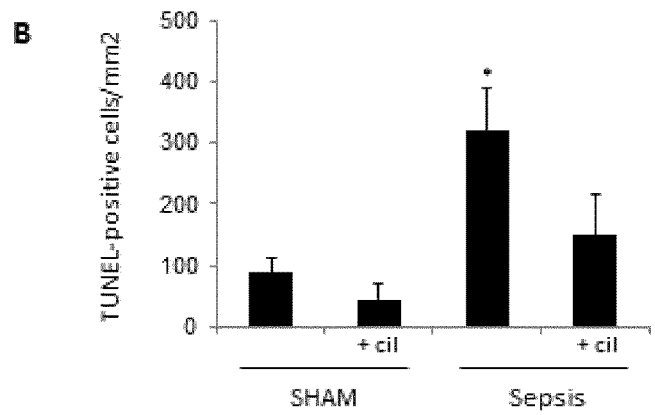

FIG. 7. Cilastatin decreases tubular cell apoptosis in kidneys of septic rats. A) Photomicrographs of TUNEL staining in the kidneys of the groups. Green fluorescent staining indicates TUNEL-positive nuclei, and blue staining (DAPI) represents all nuclei in the sample (magnification 20×). B) Quantitative analysis of TUNEL-positive cells. Results are expressed as mean±SEM; n=8-10 animals per group. *P≤0.05 vs. all other groups.

Figure 8:
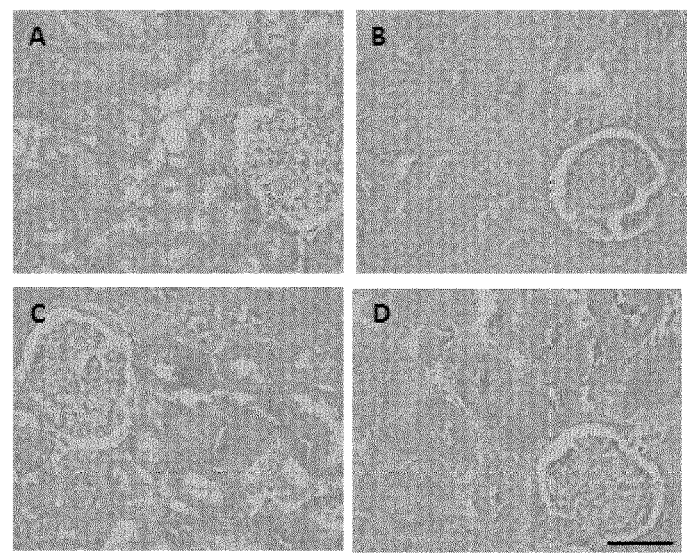
Figure 8:
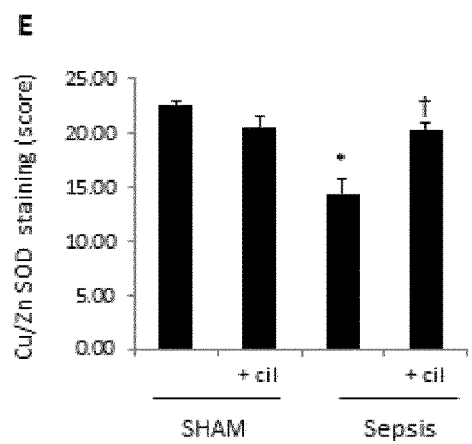
Figure 9:
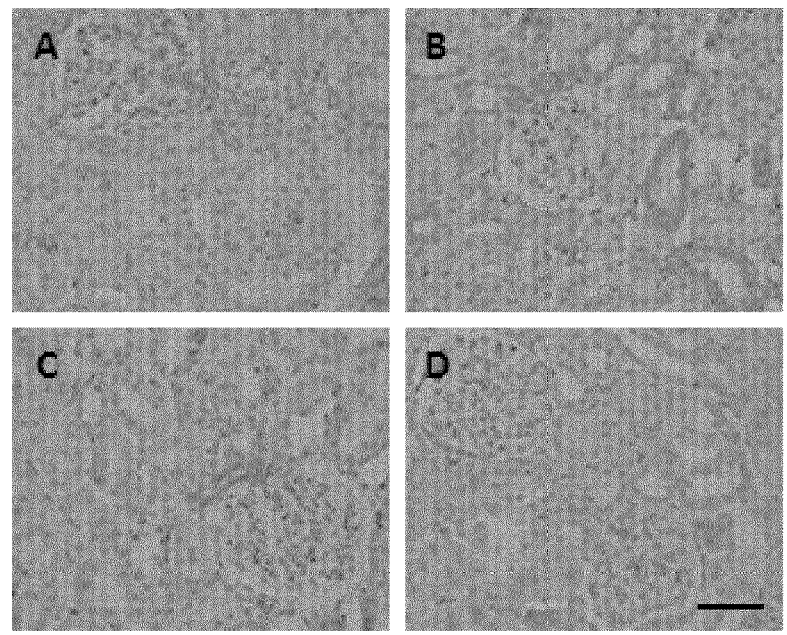
Figure 9:
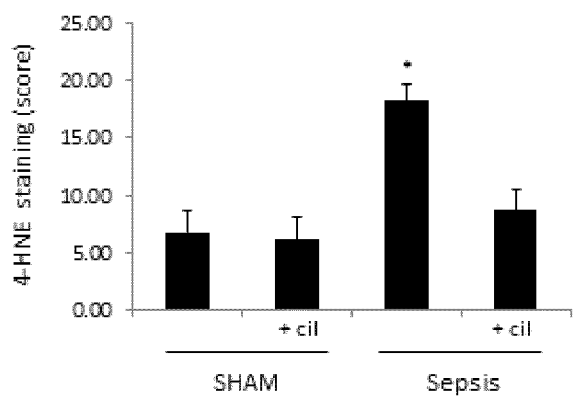

FIG. 8. Cilastatin decreases sepsis-induced oxidative stress increasing antioxidant defenses. Localization of Cu/Zn superoxide dismutase (SOD) in kidney sections. A) sham; B sepsis group; C) sham+cilastatin; and D) sepsis+cilastatin. Cilastatin significantly increased expression of Cu/Zn SOD previously diminished by sepsis (magnification, ×20). E) Semiquantification of Cu/Zn SOD immunostaining in kidney samples. F) Representative Western blot of Cu/Zn SOD in renal cortex of the different groups. G) Measurement of the antioxidant capacity in urine by specific ELISA kit. Antioxidant capacity concentration was lower in septic rats than in septic rats treated with cilastatin and control rats. All results are expressed as mean±SEM; n=8-10 animals per group. *P≤0.005, ‡≤0.01; †≤0.05 vs. all other groups; †P<0.05 vs. Sham group. Bar, 100 μm FIG. 9. Cilastatin decreases sepsis-induced lipid peroxidation. Localization of 4-HNE in kidney sections of A) sham, B) sepsis group, C) sham+cilastatin, and D) sepsis+cilastatin. Note increased tubular staining in septic rats compared with sepsis+cilastatin and sham rats (magnification, ×20). E) Semi-quantification of 4-HNE immunostaining in renal cells. All results are expressed as mean±SEM; n=8-10 animals per group. *P<0.0001 vs. all other groups. Bar, 100 μm.

Figure 10:
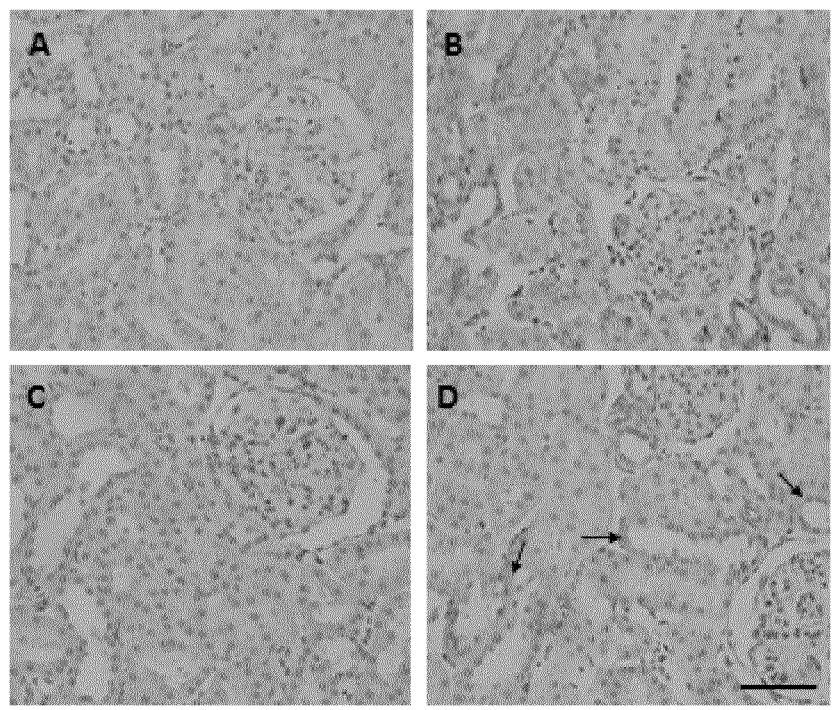
Figure 10:
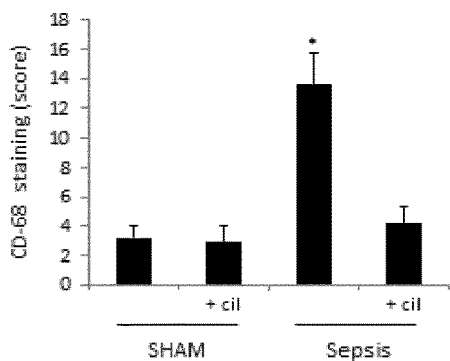

FIG. 10. Effects of cilastatin on sepsis-induced monocyte/macrophage infiltration. Localization of CD68 (monocyte/macrophage) in kidney sections of (A) sham rats, (B) sepsis, (C) sham+cilastatin, and (D) sepsis+cilastatin. Note increased staining in septic rats compared with sepsis+cilastatin and sham rats (arrow; magnification 20×); bar=100 μm. (E) Quantification of CD68 immunostaining in renal cells. All results are expressed as mean±s.e.m.; n=8-10 animals per group. *p<0.001 vs. all groups. Cil, cilastatin.

Figure 11:
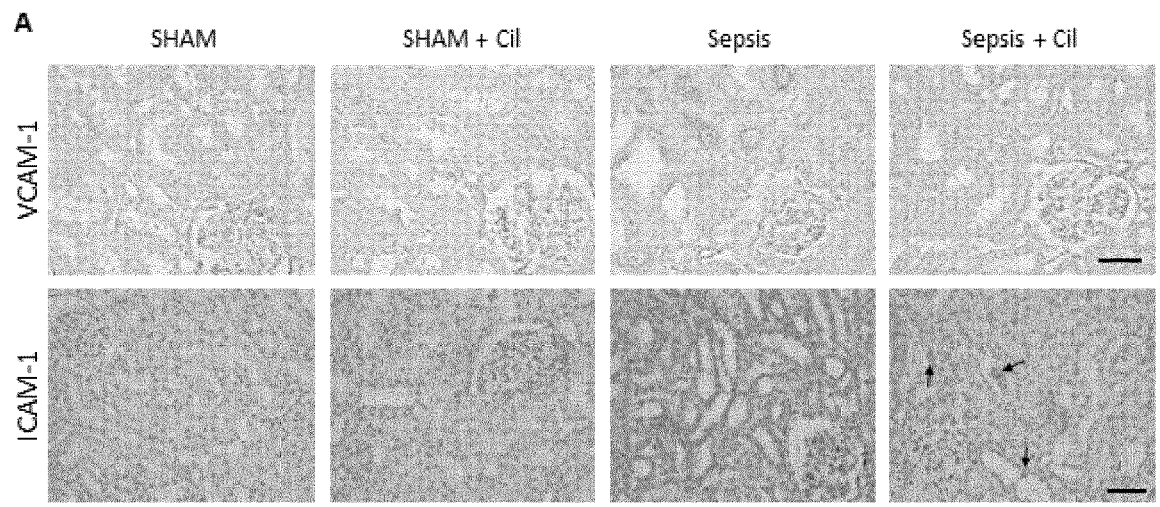
Figure 11:
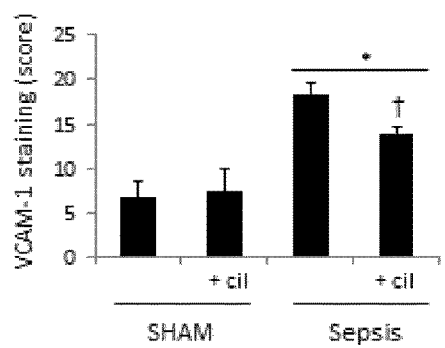
Figure 11:
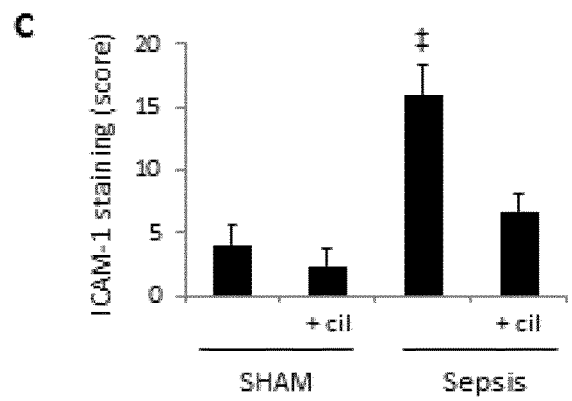

FIG. 11. Effects of sepsis and cilastatin in renal ICAM-1 and VCAM-1. A) Localization of VCAM-1 and ICAM-1 respectively in kidney sections. Note increased renal staining in both molecules in septic rats compared with sepsis+cilastatin and control groups (magnification 20×). B and C) Semiquantification of VCAM-1 and ICAM-1 immunostaining in renal cells respectively. All results are expressed as mean±s.e.m.; n=8-10 animals per group. *p≤0.01 vs. sham and sham+cilastatin groups; †p<0.05 vs. sepsis group; ‡p<0.001 vs. all other groups. Cil, cilastatin.

Figure 12:
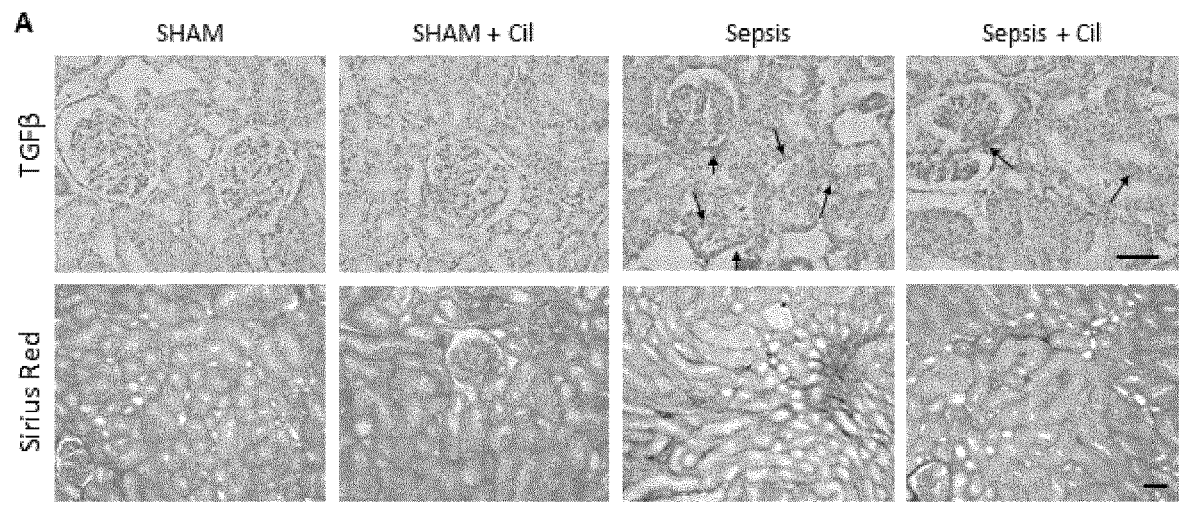
Figure 12:
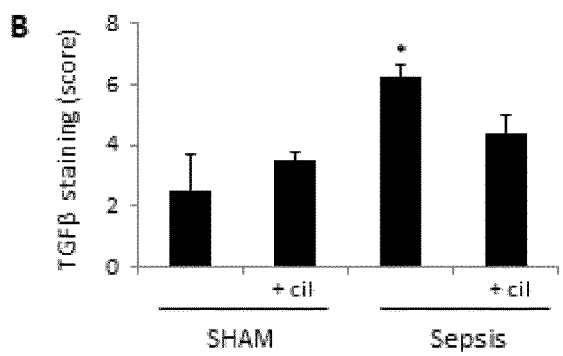
Figure 12:
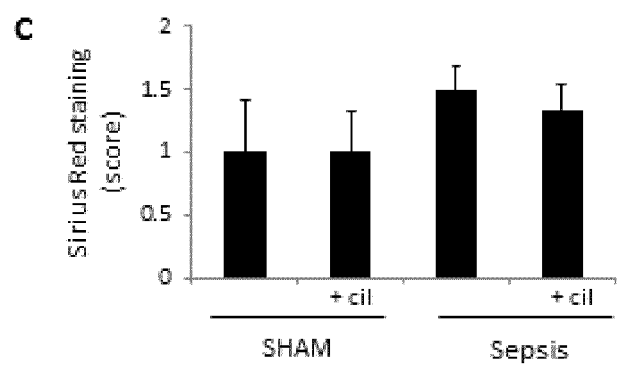

FIG. 12. Effects of cilastatin on sepsis-induced induced TGFβ increase. A) Localization of TGFβ and fibrosis (by staining with Sirius red) respectively in kidney sections. Note increased tubular TGFβ staining in septic rats (arrows) compared with sepsis+cilastatin and sham rats (magnification 20×); bar=100 μm. Collagen fibers were similar in all groups (magnification 10×, bar, 100 μm). B and C) Semi-quantification of TGFβ and Sirius red immunostaining in renal cells respectively. All results are expressed as mean±s.e.m.; n=8-10 animals per group. *p<0.05 vs. all groups. Cil, cilastatin.

Figure 13:
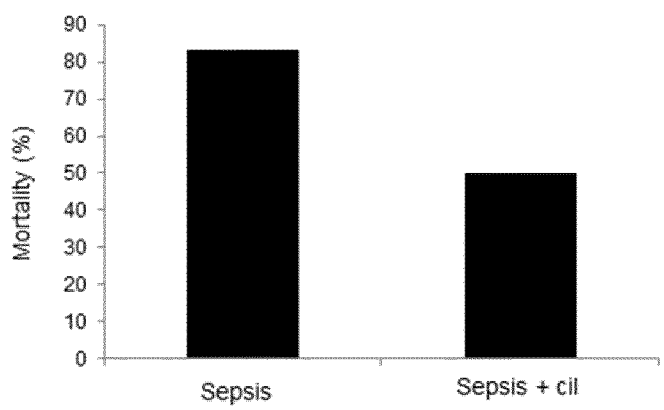

FIG. 13. Rat mortality rates after cecal ligation and puncture (CLP). Cilastatin treatment improves survival in rats subjected to CLP-induced sepsis. Mortality was monitored for 48 h after CLP procedure. Results are expressed as % of mortality in each of the groups: Mortality (%): sepsis: 83%; sepsis+cil: 50%. There were 6 rats per group.

DETAILED DESCRIPTION OF THE INVENTION

Definitions

The term "sepsis" as used herein refers to a deleterious systemic inflammatory response to infection, formally defined as the presence (probable or documented) of infection together with systemic manifestations of infection (see Table 1 below from the "international guidelines for management of severe sepsis and septic shock 2012"). The term sepsis as used herein encompasses complications thereof such as "severe sepsis" and "septic shock".

TABLE 1

Diagnostic Criteria for Sepsis
Infection, documented or suspected, and some of the following:

General variables

Fever (>38.3° C.)
Hypothermia (core temperature < 36° C.)
Heart rate > 90/min$^{-1}$ or more than two SD above the normal value for age
Tachypnea
Altered mental status
Significant edema or positive fluid balance (>20 mL/kg over 24 hr)
Hyperglycemia (plasma glucose >140 mg/dL or 7.7 mmol/L) in the absence of diabetes
Inflammatory variables Leukocytosis (WBC count > 12,000 μL$^{-1}$)
Leukopenia (WBC count < 4000 μL$^{-1}$)

TABLE 1-continued

Diagnostic Criteria for Sepsis
Infection, documented or suspected, and some of the following:

Normal WBC count with greater than 10% immature forms
Plasma C-reactive protein more than two SD above the normal value
Plasma procalcitonin more than two SD above the normal value
Hemodynamic variables Arterial hypotension (SBP < 90 mmHg, MAP < 70 mmHg, or an SBP decrease > 40 mmHg in adults or less than two SD below normal for age)
Organ dysfunction variables Arterial hypoxemia ($Pao_2/Flo_2$ < 300)
Acute oliguria (urine output < 0.5 mL/kg/hr for at least 2 hrs despite adequate fluid resuscitation)
Creatinine increase >0.5 mg/dL or 44.2 µmol/L
Coagulation abnormalities (INR > 1.5 or aPTT > 60 s)
Ileus (absent bowel sounds)
Thrombocytopenia (platelet count < 100,000 $\mu L^{-1}$)
Hyperbilirubinemia (plasma total bilirubin > 4 mg/dL or 70 µmol/L)
Tissue perfusion variables Hyperlactatemia (>1 mmol/L)
Decreased capillary refill or mottling WBC = white blood cell;
SEP = systolic blood pressure;
MAP = mean arterial pressure;
INR = international normalized ratio;
aPTT = activated partial thromboplastin time.
Diagnostic criteria for sepsis in the pediatric population are signs and symptoms of inflammation plus infection with hyper- or hypothermia (rectal temperature > 38.5° or <35° C.), tachycardia (may be absent in hypothermic patients), and at least one of the following indications of altered organ function: altered mental status, hypoxemia, increased serum lactate level, or bounding pulses.
Adapted from Levy M M, Fink M P, Marshall J C, et al: 2001 SCCM/ESICM/ACCP/ATS/SIS International Sepsis Definitions Conference. Crit Care Med 2003; 31: 1250-1256.

The term "severe sepsis" as used herein is defined as sepsis plus sepsis-induced organ dysfunction or tissue hypoperfusion (see Table 2 below from the "international guidelines for management of severe sepsis and septic shock 2012").

TABLE 2

Severe Sepsis
Severe sepsis definition = sepsis-induced tissue hypoperfusion or organ dysfunction (any of the following thought to be due to the infection)

Sepsis-induced hypotension
Lactate above upper limits laboratory normal
Urine output <0.5 mL/kg/hr for more than 2 hrs despite adequate fluid resuscitation
Acute lung injury with $Pao_2/Flo_2$ < 250 in the absence of pneumonia as infection source
Acute lung injury with $Pao_2/Flo_2$ < 200 in the presence of pneumonia as infection source
Creatinine >2.0 mg/dL (176.8 µmol/L)
Bilirubin >2 mg/dL (34.2 µmol/L)
Platelet count <100,000 µL
Coagulopathy (international normalized ratio >1.5)

Adapted from Levy M M, Fink M P, Marshall J C, et al: 2001 SCCM/ESICM/ACCP/ATS/SIS International Sepsis Definitions Conference. Crit Care Med 2003; 31: 1250-1256.

Sepsis-induced hypotension is defined as a systolic blood pressure (SBP)<90 mm Hg or mean arterial pressure (MAP) <70 mm Hg or a SBP decrease >40 mm Hg or less than two standard deviations below normal for age in the absence of other causes of hypotension. Septic shock is defined as sepsis-induced hypotension persisting despite adequate fluid resuscitation.

Sepsis-induced tissue hypoperfusion is defined as infection-induced hypotension, elevated lactate, or oliguria.

The term "sepsis-associated acute kidney injury" (SA-AKI) or "septic AKI" as used herein refers to acute kidney injury (AKI) in the presence of sepsis.

The term "treatment" as used herein refers to the prophylactic and/or therapeutic treatment.

The term "therapeutic treatment" as used herein refers to bringing a body from a pathological state or disease back to its normal, healthy state. Specifically, unless otherwise indicated, includes the amelioration, cure, and/or maintenance of a cure (i.e., the prevention or delay of relapse) of a disease or disorder. Treatment after a disorder has started aims to reduce, alleviate, ameliorate or altogether eliminate the disorder, and/or its associated symptoms, to prevent it from becoming worse, to slow the rate of progression, or to prevent the disorder from re-occurring once it has been initially eliminated (i.e., to prevent a relapse). It is noted that, this term as used herein is not understood to include the term "prophylactic treatment" as defined herein.

The term "prophylactic treatment" or "preventive treatment" as used herein refers to preventing a pathological state. It is noted that, this term as used herein is not understood to include the term "therapeutic treatment" as defined herein.

The term "effective amount" as used herein refers to an amount that is effective, upon single or multiple dose administration to a subject (such as a human patient) in the prophylactic or therapeutic treatment of a disease, disorder or pathological condition.

The term "subject" as used herein refers to a mammalian subject. Preferably, it is selected from a human, companion animal, non-domestic livestock or zoo animal. For example, the subject may be selected from a human, mouse, rat, dog, cat, cow, pig, sheep, horse, bear, and so on. In a preferred embodiment, said mammalian subject is a human subject.

The term "combination" or "combination therapy" as used throughout the specification, is meant to encompass the administration of the referred therapeutic agents to a subject suffering from a disease, disorder or pathological condition, in the same or separate pharmaceutical formulations, and at the same time or at different times. If the therapeutic agents are administered at different times they should be administered sufficiently close in time to provide for the potentiating or synergistic response to occur. In such instances, it is contemplated that one would typically administer both therapeutic agents within about 12-24 hours of each other and, more preferably, within about 6-12 hours of each other. In some situations, it may be desirable to extend the time period for treatment significantly, however, where several days (2, 3, 4, 5, 6 or 7) to several weeks (1, 2, 3, 4, 5, 6, 7 or 8) lapse between the respective administrations. In other situations, it might be desirable to reduce the time between administration, administering both therapeutic agents within seconds or minutes to hours, preferably within about 6 hours from each other, more preferably within about 1 or 3 hours.

The term "single agent" as used herein relates to the use of an active ingredient sufficiently separate in time from another active ingredient to prevent for the potentiating or synergistic response to occur. More specifically, the use as "single agent" does not encompass the use as a "combination therapy".

The term "active ingredient" as used herein refers to any component that provides pharmacological activity.

The term "pharmaceutically acceptable salt" as used herein refers to the relatively non-toxic, inorganic and organic acid addition salts of compounds as described herein. These salts can be prepared in situ during the final isolation and purification of the compounds or by separately reacting the purified compound in its free base form with a suitable organic or inorganic acid and isolating the salt thus formed. Representative salts include the hydrobromide, hydrochloride, sulfate, bisulfate, nitrate, acetate, oxalate, valerate, oleate, palmitate, stearate, laurate, borate, benzoate, lactate, phosphate, tosylate, citrate, maleate, fumarate, succinate, tartrate, naphthylate mesylate, glucoheptonate, lactobsonate, and laurylsulphonate salts, and the like. These may include cations based on the alkali and alkaline earth metals, such as sodium, lithium, potassium, calcium, magnesium, and the like, as well as non-toxic ammonium, quaternary ammonium, and amine cations including, but not limited to ammonium, tetramethylammonium, tetraethylammonium, methylamine, dimethylamine, trimethylamine, triethylamine, ethylamine, and the like (see, for example, Berge S. M, et al, "Pharmaceutical Salts," J. Pharm. Sci., 1977; 66:1-19 which is incorporated herein by reference.)

The term "prodrug" as used herein refers to inactive, bioreversible derivatives of the compounds as described herein. Generally, these must undergo an enzymatic and/or chemical transformation in vivo to release the active parent compound, which can then elicit its desired pharmacological effect in the body. Prodrugs are typically designed to overcome formulation, delivery, and toxicity problems. A thorough discussion of prodrugs is provided in T. Higuchi and V. Stella, "Pro-drugs as Novel Delivery Systems," Vol. 14 of the A.C.S. Symposium Series; in Bioreversible Carriers in Drug Design, ed. Edward B. Roche, American Pharmaceutical Association and Pergamon Press, 1987; and in Rautio et al., Nature Reviews Drug Discovery 2008, 7, 255-270.

The terms "agent" and "drug" are used herein interchangeably.

Detailed Description

The first aspect of the invention relates to cilastatin for use in a preventive or therapeutic method of treating sepsis in a mammalian subject, with the proviso that when cilastatin is administered in combination with another drug said other drug is not imipenem (i.e. cilastatin is not administered in combination with imipenem). In a preferred embodiment, the invention relates to the use of cilastatin in a method for the therapeutic treatment of sepsis.

In addition, the present invention provides a method of treating sepsis comprising administering to a subject in need of such treatment a prophylactic or therapeutically effective amount of cilastatin, with the proviso that when cilastatin is administered in combination with another drug said other drug is not imipenem (i.e. cilastatin is not administered in combination with imipenem).

It further provides the use of cilastatin in the manufacture of a medicament for the preventive or therapeutic treatment of sepsis, with the proviso that when cilastatin is administered in combination with another drug said other drug is not imipenem (i.e. cilastatin is not administered in combination with imipenem.

In a particular embodiment of any of the above, when cilastatin is administered in combination with another drug, said other drug is not a beta-lactam antibiotic.

The term "cilastatin" as used herein refers to (Z)-7-[(2R)-2-Amino-3-hydroxy-3-oxopropyl]sulfanyl-2-{[(1S)-2,2-dimethylcyclopropanecarbonyl]amino}hept-2-enoic acid of formula:

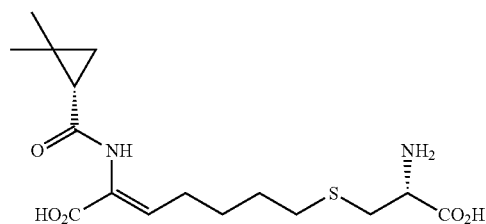

It encompasses the crystalline form and any pharmaceutical salts, solvates or prodrugs thereof.

Typically cilastatin has been used in the sodium salt form. Cilastatin and related dehydropeptidase-I (DHP-I) inhibitors are disclosed for example in U.S. Pat. No. 4,668,504 which is herein incorporated by reference.

The term "imipenem" as used herein refers to the beta-lactam antibiotic (5R,6S)-6-[(1R)-1-hydroxyethyl]-3-({2-[(iminomethyl)amino]ethyl}thio)-7-oxo-1-azabicyclo[3.2.0]hept-2-ene-2-carboxylic acid of formula:

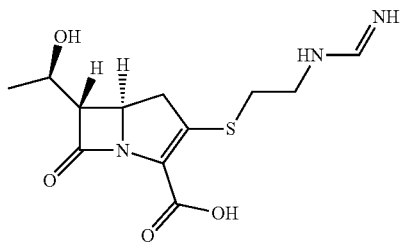 [SMILES: C[C@@H](O)[C@H]1C(=O)N2C(C(=O)O)=C(SCCNC=N)C[C@H]12]

It encompasses the crystalline form and any pharmaceutical salts or solvates thereof. Typically, imipenem has been used in the form of imipenem monohydrate. For example Tienam® 500 mg contained imipenem monohydrate corresponding to 500 mg of imipenem and the sodium salt of cilastatin corresponding to 500 mg of cilastatin.

Sepsis and the complications thereof referred as "severe sepsis" and "septic shock" have been described above. In a particular embodiment of the method of treatment of the invention said subject suffers or is at risk of suffering from severe sepsis and/or septic shock. Preferably, said subject suffers from severe sepsis (e.g. severe sepsis with multiple organ failure) and/or septic shock.

Regardless of the degree of severity, said sepsis or septicemia may have bacterial, fungal and/or viral origin. Also, septicemia may be caused by a single microbial species or by more than one microbial species which is referred as polymicrobial septicemia, for instance a polymicrobial bacteremia. In a preferred embodiment, said sepsis is a polymicrobial septicemia.

As referred above, sepsis, especially where it has evolved to severe sepsis and/or sepsis shock, is characterized by a high mortality rate and the speed and appropriateness of therapy administered promptly after severe sepsis develops has been described as essential for a positive outcome. Cilastatin has shown to significantly reduce mortality associated to sepsis in a cecal ligation puncture (CLP) induced sepsis model (see Example 3 and FIG. 13).

Regardless of the severity of sepsis (preferably in severe sepsis and/or septic shock settings), in a particular embodiment of the method of treating sepsis of the invention cilastatin is capable of preventing or reducing death by sepsis. In a preferred embodiment, it is capable of preventing or reducing death by sepsis in a cecal ligation puncture (CLP)-induced sepsis animal model. The CLP model comprises the perforation of the cecum allowing the release of fecal material into the peritoneal cavity of the animal to generate an exacerbated immune response induced by polymicrobial infection. The CLP model has previously been described as a preferred animal model for the study of human sepsis. Indeed, it has been reported to more closely reproduce human sepsis than simple administration of lipopolysaccharide and to induce an early hyperdynamic phase characterized by decreased peripheral vascular resistance and increased cardiac output (Ronco et al., Clin J Am Soc Nephrol 2008, 3: 531-544; Toscano M. G, et al., J. Vis. Exp. 2011, 51, e2860).

Figure 3:
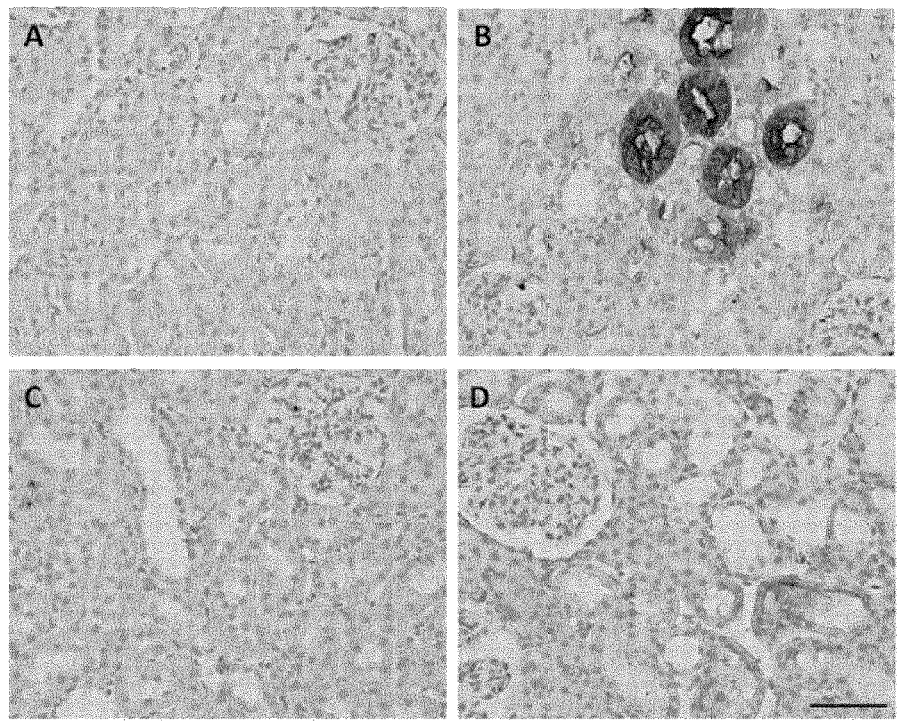
FIG. 3. Effect of cilastatin on the kidney tissue levels of the renal failure biomarker KIM-1. Localization of KIM-1 in kidney sections: (A) sham, (B) sepsis, (C) sham+cilastatin, (D) sepsis+cilastatin (magnification 20×), bar=100 μm. Cilastatin significantly reduced the increase of KIM-1 caused by CLP-induced sepsis); (E) Semi-quantification of KIM-1 immunostaining in renal cells. (F) Representative Western blot of KIM-1 in renal cortex and (G) densitometric analysis of Western blot of KIM-1. Cilastatin significantly reduced the increase of KIM-1 caused by CLP-induced sepsis. Results are expressed as mean±s.e.m.; n=8-10 animals per group. †p≤0.01, *p<0.001 vs. all groups. KIM-1 (Kidney injury molecule-1); Cil, (cilastatin); a.u. (arbitrary units).
Figure 3:
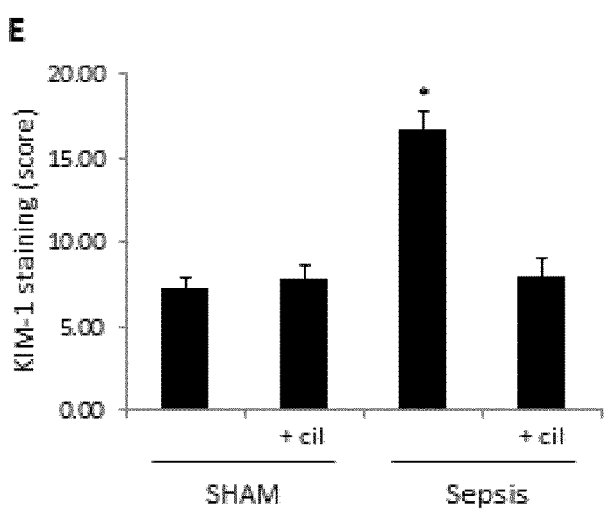
Figure 3:
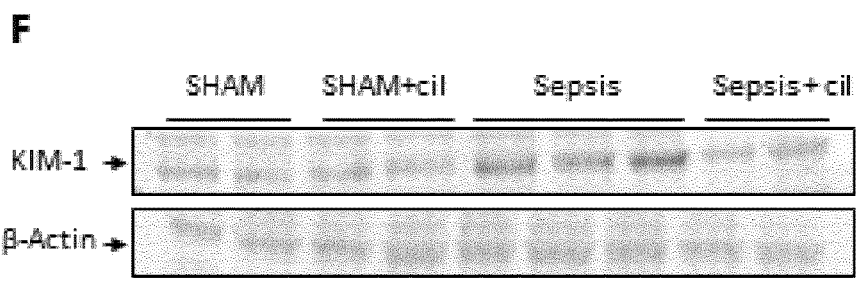
Figure 3:
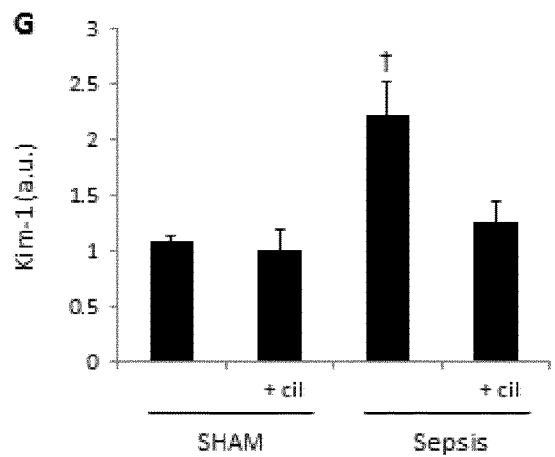
Figure 4:
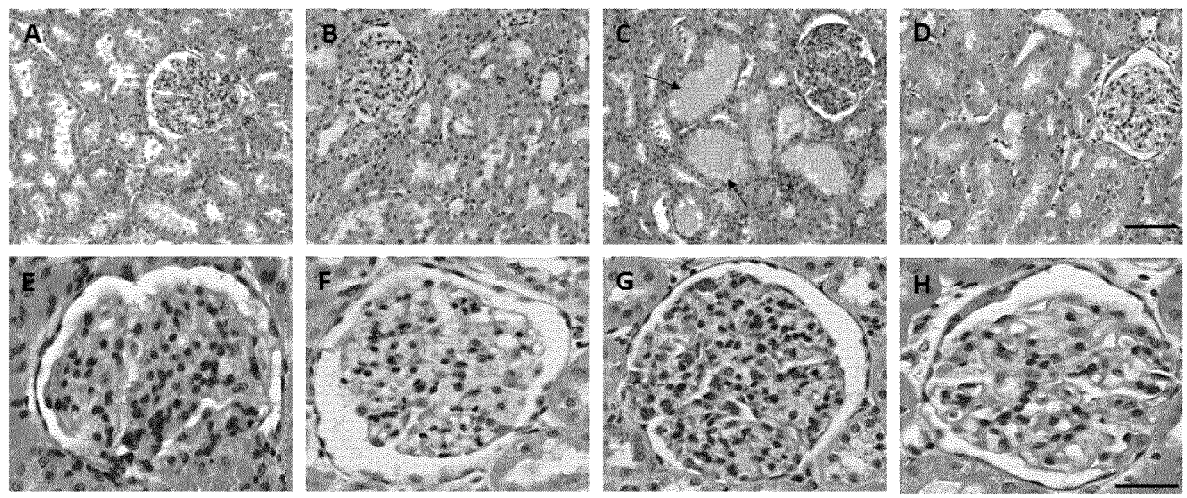
FIG. 4. Histopathological sepsis-associated renal injury. Representative images of the renal pathology (hematoxylin-eosin staining, magnification, ×20) at day 2 after CLP surgery induced sepsis. A) sham rats, B) sham+cilastatin, C) sepsis group and D) sepsis+cilastatin. Control groups show normal renal structure; CLP-induced sepsis kidneys show marked injury with leukocyte infiltration (asterisk) loss of brush border, dilation of tubules, and intratubular cast formation (arrows). These changes were significantly reduced by treatment with cilastatin. E-H) Details of glomeruli of sham group (E), sham+cilastatin (F), sepsis group (G) and sepsis+cilastatin (H). A major capillary congestion of the glomerulus can be observed in sepsis group. Cilastatin decreased damage. A-D images, bar=100 μm; E-H images, bar=50 μm. I) Semiquantitative renal injury score. Results are expressed as mean±s.e.m.; n=8-10 animals per group. *p<0.01 vs. all groups. Cil, cilastatin.
Figure 4:
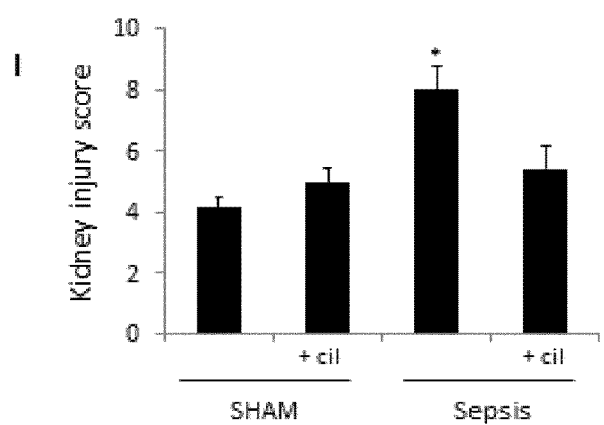

As referred above, the inventors have shown the positive effects of cilastatin in the treatment of septic AKI in a cecal ligation puncture (CLP) induced sepsis model. In particular, the sepsis model treated with vehicle showed 48 hours after induction of sepsis an increase of serum creatinine, BUN and urinary protein levels and a reduction of glomerular filtration rate with respect to sham-operated control rats. Conversely, cilastatin was shown to decrease markers of renal function such as creatinine or BUN previously elevated by sepsis (FIG. 2), as well as KIM-1, a novel early biomarker of AKI whose levels are elevated in patients with sepsis (Tu Y et al, Ren Fail. 2014; 36(10):1559-63) (FIG. 3). In addition, cilastatin significantly reduced histological damage in renal tissues (FIG. 4). It has further shown effects in reducing apoptosis (FIGS. 5-7), ameliorating kidney cells antioxidant capacity (FIGS. 8-9), and decreasing inflammation (FIGS. 10-11) and fibrosis (FIG. 12).

In a particular embodiment of the method of treatment of the invention, cilastatin is administered to a subject suffering or at risk of suffering from septic AKI. Acute kidney injury (AKI) in the setting of sepsis is referred herein as "septic AKI" or sepsis-associated AKI (SA-AKI)". In a more specific embodiment, cilastatin is administered to a subject suffering from sepsis or at risk of suffering from septic AKI.

In a preferred embodiment, cilastatin is capable of preventing or reducing septic AKI. In a more preferred embodiment, it is capable of preventing or reducing septic AKI in a cecal ligation puncture (CLP)-induced sepsis animal model.

The invention also relates to cilastatin for use in a preventive or therapeutic method of treating sepsis-associated acute kidney injury in a mammalian subject. Preferably, it relates to a method of treating septic AKI wherein said method is characterized by reducing mortality. Preferred features and embodiments are as defined herein for other aspects of the invention.

The invention further refers to cilastatin for use in a method for reducing mortality in a mammalian subject which suffers or is at risk of suffering from sepsis, preferably which suffers or is at risk of suffering from SA-AKI. Preferred features and embodiments are as defined herein for other aspects of the invention.

The present invention relates to the treatment of a mammalian subject. Preferably, said mammalian subject is a human subject. This human subject may be an adult subject or a child. The child population is typically defined as those patients who are under 18 years. In a particular embodiment said patients are between 0 and 15 years, more preferably between 2 and 12 years. Elderly patients suffering from sepsis have been identified as a high risk population of SA-AKI (Alobaidi et al., Seminars in nephrology 2015, 35(1), 2-11). In a particular embodiment of the method of treatment of the invention, the subject is a human adult, preferably older than 60 years, more preferably older than 65 years.

Septic patients suffering from other diseases, specifically chronic kidney disease, diabetes mellitus, hypertension, heart failure, malignancy, and liver disease have also been described as presenting an increased susceptibility to septic AKI (Bagshaw et al. Crit. Care 2008, 12:R47; Bagshaw et al., Clin J Am Soc Nephrol. 2007; 2:431-9). Thus, in a particular embodiment of the method of treatment of the invention cilastatin is administered to a subject suffering or having suffered from co-morbidities, preferably suffering or having suffered from a disease selected from the group consisting of chronic kidney disease, diabetes mellitus, hypertension, heart disease, cancer and liver disease.

Sepsis may have different primary sources of infection. An increased risk of suffering from septic-AKI has also been related to the primary source of infection. In particular, blood stream infection, abdominal and genitourinary sepsis, and infective endocarditis, have been associated with a higher likelihood of developing AKI (Godin et al., Seminars in nephrology 2015, 35(1), 12-22; Bagshaw et al., Intensive Care Med. 2009; 35:871-81). In a particular embodiment of the method of treatment of the invention, the sepsis is characterized by the primary site of infection being selected from the group consisting of blood, the abdominal cavity, the genitourinary tract or the heart. Preferably, said primary site of infection is the abdominal cavity and/or the gastrointestinal tract.

A Pharmaceutical Composition for Use in the Method of Treatment of the Invention The present invention also provides a pharmaceutical composition comprising cilastatin and a pharmaceutically acceptable excipient, for use in a method of treatment as defined herein. In a particular embodiment, said pharmaceutical composition comprises cilastatin as a single active ingredient.

In another particular embodiment, said pharmaceutical composition comprises cilastatin and another drug, preferably another drug other than imipenem. The list of drugs which may be combined with cilastatin in a pharmaceutical composition is not particularly limited. Illustrative non-limiting examples of drug combinations are provided below.

In a preferred embodiment, said other drug is an antimicrobial agent, preferably an antimicrobial agent other than imipenem. Said antimicrobial agent may or may not be nephrotoxic.

In a more preferred embodiment, said antimicrobial agent, preferably other than imipenem, is a nephrotoxic antimicrobial agent with the proviso that it is not a nephrotoxic antimicrobial agent selected from the group consisting of polymyxins, beta-lactams, aminoglycosides, glycopeptides, and polyenes. In a more preferred embodiment, said nephrotoxic antimicrobial agent is not a beta-lactam antibiotic. The terms "beta-lactam nephrotoxic antimicrobial agent" and "beta-lactam antibiotic" are used herein interchangeably.

In another more preferred embodiment, said antimicrobial agent, preferably other than imipenem, is a nephrotoxic antimicrobial agent with the proviso that it is not a nephrotoxic antimicrobial agent selected from the group consisting of gentamicin; kanamycin; tobramycin; amikacin; netilmicin; bacitracin; neomycin; metronidazole; polymyxin B; polymyxin E (colistin), trimethoprim; sulfisoxazole; sulfamethoxazole; methenamine; vancomycin; spectinomycin; chloramphenicol; amphotericin B, pentamidine, pentamidine isoethionate; atavaquone; rifampin; paraaminosalicylic acid; isoniazid; capreomycin; acyclovir; AZT; 3TC; vidarabine; cidofovir; lamivudine; saquinavir and valacyclovir.

Other embodiments of the combination treatment are provided below.

Pharmaceutically acceptable excipients include, but are not limited to a carrier or diluent, such as a gum, a starch (e.g. corn starch, pregeletanized starch), a sugar (e.g. lactose, mannitol, sucrose, dextrose), a cellulosic material (e.g. microcrystaline cellulose), an acrylate (e.g. polymethylacrylate), calcium carbonate, magnesium oxide, talc, or mixtures thereof; a binder (e.g. acacia, cornstarch, gelatin, carbomer, ethyl cellulose, guar gum, hydroxypropyl cellulose, hydroxypropyl methyl cellulose, povidone); a disintegrating agent (e.g. cornstarch, potato starch, alginic acid, silicon dioxide, croscarmelose sodium, crospovidone, guar gum, sodium starch glycolate), a buffer (e.g. Tris-HCl, acetate, phosphate, bicarbonate) of various pH and ionic strength; and additive such as albumin or gelatin to prevent absorption to surfaces; a detergent (e.g. Tween 20, Tween 80, Pluronic F68, bile acid salts); a protease inhibitor; a surfactant (e.g. sodium lauryl sulfate); a permeation enhancer; a solubilizing agent (e.g. glycerol, polyethylene glycerol); an antioxidants (e.g. ascorbic acid, sodium metabisulfite, butylated hydroxyanisole); a stabilizer (e.g. hydroxypropyl cellulose, hydroxypropylmethyl cellulose); a viscosity increasing agent (e.g. carbomer, colloidal silicon dioxide, ethyl cellulose, guar gum); a sweetener (e.g. aspartame, citric acid); a preservative (e.g. thimerosal, benzyl alcohol, parabens); a lubricant (e.g. stearic acid, magnesium stearate, polyethylene glycol, sodium lauryl sulfate); a flow-aid (e.g. colloidal silicon dioxide), a plasticizer (e.g. diethyl phthalate, triethyl citrate); an emulsifier (e.g. carbomer, hydroxypropyl cellulose, sodium lauryl sulfate); a polymer coating (e.g. poloxamers or poioxamines); a coating and film forming agent (e.g. ethyl cellulose, acrylates, polymethacrylates); a pharmaceutically acceptable carrier for liquid formulations, such as an aqueous (water, alcoholic/aqueous solution, emulsion or suspension, including saline and buffered media) or non-aqueous (e.g., propylene glycol, polyethylene glycol, and injectable organic esters, such as ethyl oleate) solution, suspension, emulsion or oil; and a parenteral vehicle (e.g., for subcutaneous, intravenous, intraarterial, or intramuscular injection), including but not limited to, water, oils, saline solution, Ringer's dextrose, aqueous dextrose and other sugar solutions. A pharmaceutically acceptable excipient also includes excipients for nanoencapsulation purposes, such as a cationic polyelectrolyte (e.g. gelatin and an anionic polyelectrolyte (e.g. arabic gum).

In a particular embodiment, said formulation comprises or consists of cilastatin and sodium bicarbonate as a buffer.

Route of Administration

Cilastatin for use in a method of treatment of the invention is typically formulated as a pharmaceutical composition to be compatible with its intended route of administration. Methods to accomplish the administration are known to those of ordinary skill in the art. This includes, for example, injection or infusion, by parenteral routes such as intravenous, intravascular, intraarterial, subcutaneous, intramuscular, intraperitoneal, intraventricular, intraepidural, or others as well as oral, sublingual, nasal, ophthalmic, rectal, transdermal or topical. Sustained release administration is also specifically contemplated, e.g., as depot injections or erodible implants. Localized delivery is particularly contemplated, e.g., as delivery via a catheter to one or more arteries, such as the renal artery or a vessel supplying a localized site of interest.

In a particular embodiment, cilastatin is administered by the oral, sublingual, transdermal or parenteral route. Preferably, cilastatin is administered by the intramuscular, intraperitoneal or intravascular route of administration, e.g., by the intravenous route. Administration by the intravascular route is carried out using devices well known in the art, which are used to administer fluids from a container to a patient's vascular system through a needle or catheter inserted into a vein. The device may include the needle or catheter, tubing, a flow regulator, a drip chamber, an infusion line filter, an I.V. set stopcock, fluid delivery tubing, connectors between parts of the set, a side tube with a cap to serve as an injection site, and a hollow spike to penetrate and connect the tubing to an I.V. bag or other infusion fluid container.

Preferably, said composition is in a form suitable for intravascular administration. In a preferred embodiment, said composition is an aqueous composition, more preferably a stable aqueous composition. As used herein, a "stable composition" may refer to a formulation in which the active ingredient therein essentially retains its physical stability and/or chemical stability and/or biological activity upon storage.

Typically, cilastatin is formulated, preferably as single agent or single active ingredient, in a buffered solution adjusted in the pH range of 6.5-8.5. Suitable diluents include but are not limited to 0.9% sodium chloride injection; 5% or 10% dextrose injection; 5% dextrose and 0.9% sodium chloride injection; 5% dextrose injection with 0.225% or 0.45% saline solution; 5% dextrose injection with 0.15% potassium chloride solution; mannitol 5% and 10%. In a preferred embodiment, said diluent is 0.9% sodium chloride injection; or 5% dextrose injection.

Some embodiments of such compositions may be provided by lyophilised formulations. Said lyophilised formulations can be reconstituted and diluted to give a composition of this invention in the form of a solution ready for intravascular injection. By way of illustration, but not as limitations, embodiments of lyophilised formulations according to this invention are reconstituted with a volume of a diluent as described above. Preferably, said lyophilised formulations are presented in single dose (typically 250 mg or 500 mg of cilastatin) containers. The container content may be diluted in a volume of 5 to 5000 mL of diluent, preferably from 10 to 1000 mL of diluent, more preferably from 50 to 500 mL of diluent, even more preferably from 20 to 200 mL of diluent, most preferably around 100 mL of diluent.

Reconstituted embodiments of the present invention can further be diluted if so desired. This further dilution is preferably carried out with an aqueous diluent as described herein. The reconstituted solution will be diluted depending on the concentration in the reconstituted solution and the desired concentration in the diluted solution.

In a particular embodiment, the lyophilised formulation (preferably of 250 mg or 500 mg of cilastatin) is reconstituted in an aqueous diluent volume of around 10 mL and further diluted to a final volume of 100 mL. In another particular embodiment, it is directly reconstituted in an aqueous diluent volume of around 100 mL.

Typically, cilastatin will be formulated at a concentration within a range from 0.5 to 25 mg/mL, preferably from 0.75 to 10 mg/mL, most preferably around 2.5 mg/mL or around 5 mg/mL.

Administration Schedule and Dosage

Cilastatin can be administered a single time. It may also be administered regularly throughout the course of the method of treatment, for example, one, two, three, four, or more times a day, every other day, weekly, bi-weekly, every three weeks or monthly. In a particular embodiment, cilastatin is administered daily, preferably three or four times per day, from the diagnosis of sepsis or suspected sepsis until sepsis remittance. Cilastatin may also be administered continuously to the subject (e.g, intravenously or by release from an implant, pump, sustained release formulation, etc.).

The dosage to be administered can depend on multiple factors, including the type and severity of the disease and/or on the characteristics of the subject, such as general health, age, sex, body weight and tolerance to drugs and should be adjusted, as needed, according to individual need and professional judgment. The dosage may also vary depending upon factors, such as route of administration, treatment regime, target site, or other therapies administered. The skilled artisan will be able to determine appropriate doses depending on these and other factors. A prophylactic or therapeutically effective amount may include, but is not limited to, dosage ranges of about 0.1 mg/kg to about 100 mg/kg of body weight, preferably about 10 mg/kg to about 50 mg/kg, more preferably, about 20 mg/kg to about 40 mg/kg.

In a particular embodiment, cilastatin is administered by the parenteral route of administration (preferably intravenously) at a dosage of about 10 to about 50 mg/kg of body weight, preferably of about 20 to about 40 mg/kg of body weight, more preferably of about 22 to about 26 mg/kg of body weight for a human adult and of about 34 to about 38 mg/kg of body weight for a human child.

Preferred dosage and administration schedules for a human adult are daily doses from 1 gr to 4 gr by the parenteral route (preferably intravenously), such as by giving 250 mg every 6 h, 500 mg every 6 h or 8 h, or 1 gr every 6 h or 8 h.

Cilastatin may be administered alone (as a single agent) or in combination with another drug other than imipenem.

Combination Therapies for Use in the Method of Treatment of the Invention

The invention also relates to cilastatin or the pharmaceutical composition comprising thereof for use in a method of treatment of the invention wherein administration is performed in combination with another drug, preferably with another drug other than imipenem.

Cilastatin will typically be used in combination with an antimicrobial therapy. Other drugs are often used as adjuvant therapy in patients suffering from severe sepsis and/or septic shock and may also be used in the present invention, for example: i) vasopressors such as norepinephrine, epinephrine, vasopressin, and/or dopamine to target a mean arterial pressure above 65 mmHg; ii) ionotropic agents such as dobutamine in the presence of myocardial disfunction or signs of hypoperfusion; and iii) corticosteroids such as hydrocortisone, in those cases where fluid resuscitation and vasopressor therapy are not able to restore hemodynamic stability (Surviving Sepsis Campaign Guidelines 2012).

In a particular embodiment, cilastatin is administered in combination with an antimicrobial therapy or drug as described herein. The term "antimicrobial therapy" as used herein refers to drugs for the treatment of an active infection, such as antiviral, antibacterial and antifungal drugs. These are well known by a person skilled in the art (see for instance "Gideon Guide to antimicrobial agents" Berger S., 2015 Gideon Informatics, Inc.; "Sepsis, new strategies for management", Rello J. and Restrepo M., 2008 Springer-Verlag).

Antibiotic therapy, preferably intravenously, is typically initiated within the first six hours or earlier (eg, within one hour), after obtaining appropriate cultures, since early initiation of antibiotic therapy is associated with lower mortality. The choice of antibiotics can be complex and should consider the patient's history (eg, recent antibiotics received), comorbidities, clinical context (eg, community- or hospital-acquired), Gram stain data, and local resistance patterns. Other parameters which may be considered are the site and cause of the initial infection, the organs affected and the extent of any damage (www.nhs.uk/conditions/blood-poisoning/Pages/Treatment.aspx)

When the potential pathogen or infection source is not immediately obvious, broad-spectrum antibiotic coverage directed against both gram-positive and gram-negative bacteria may be used typically based upon each patient's presenting illness and local patterns of infection. When used empirically in patients with sepsis, de-escalation for the most appropriate antibiotic therapy is recommended as soon as the bacterial susceptibility profile is known (Surviving Sepsis Campaign Guidelines 2012).

A combination therapy for use in the method of treatment of the invention may include the use of various classes of antibiotics, typically at least two different classes of antibiotics. This includes combinations of two or three antibiotics given concomitantly. Antibiotics typically used in the treatment of sepsis include aminoglycosides, macrolides, beta-lactams (e.g., penicillins; first, second, third and fourth generation cephalosporins, and carbapenems), glycopeptides, lincosamides and/or fluoroquinolones. For instance, a beta-lactam agent (e.g., a third or fourth generation cephalosporin) with a macrolide, fluoroquine or aminoglycoside is generally used for broad-spectrum coverage. In addition, combinations may also include vancomycin to treat many MRSA infections. Some of the commonly used antibiotic and antibiotic combinations are:

ceftriaxone,
meropenem,
ceftazidime,
cefotaxime,
cefepime,
piperacillin and tazobactam,
ampicillin and sulbactam,
levofloxacin,
clindamycin.

The Surviving Sepsis Campaign Guidelines 2012 suggest combination empiric therapy for neutropenic patients with severe sepsis (grade 2B) and for patients with difficult-to-treat, multidrug-resistant bacterial pathogens such as *Acinetobacter* and *Pseudomonas* spp. (grade 2B). For selected patients with severe infections associated with respiratory failure and septic shock, combination therapy with an extended spectrum beta-lactam and either an aminoglycoside or a fluoroquinolone is suggested for *P. aeruginosa* bacteremia (grade 2B). Similarly, a more complex combination of beta-lactam and a macrolide is suggested for patients with septic shock from bacteremic *Streptococcus pneumoniae* infections (grade 2B).

Antibiotic therapy has in general a duration of 7-10 days. In patients who are neutropenic, antibiotic treatment typically continues until the neutropenia has resolved or the planned antibiotic course is complete, whichever is longer, whereas in non-neutropenic patients in whom infection is excluded, antibiotics are generally discontinued to avoid the generation of antibiotic resistances.

It has been reported that nephrotoxic beta-lactam antibiotics can cause acute proximal tubular necrosis. Renal toxicity has been rare with the penicillins and uncommon with the cephalosporins, however there has been a higher incidence with the penems. In particular, the first-generation cephalosporins cephaloridine and cephaloglycin; and the carbapenems imipenem and panipenem have been described as being nephrotoxics. Indeed, imipenem and panipenem are marketed in combination with nephroprotective renal transport inhibitors, namely with cilastatin and betamipron, respectively (Tune B., Pediatric Nephrology 1997, 11(6), 768-772). Cilastatin may be used in combination with any of these agents.

In a particular embodiment, cilastatin is not administered in combination with imipenem or panipenem. In another particular embodiment, cilastatin is not administered in combination with an antibiotic selected from the list consisting of imipenem, panipenem, cephaloridine and cephaloglycin. Preferably, cilastatin is not administered in combination with a carbapenem antibiotic and/or a first generation cephalosporin. In a more particular embodiment, cilastatin is not administered in combination with a beta-lactam nephrotoxic antimicrobial agent.

In another particular embodiment, when cilastatin is administered in combination it is not administered in combination with a beta-lactam nephrotoxic antimicrobial agent and/or a non-beta-lactam nephrotoxic antimicrobial agent selected from the group consisting of, gentamicin; kanamycin; tobramycin; amikacin; netilmycin; bacitracin; neomycin; metronidazole; polymyxin B; polymyxin E (colistin), trimethoprim; sulfisoxazole; sulfamethoxazole; methenamine; vancomycin; spectinomycin; chloramphenicol; amphotericin B, pentamidine, pentamidine isoethionate; atavaquone; rifampin; paraaminosalicylic acid; isoniazid; capreomycin; acyclovir; AZT; 3TC; vidarabine; cidofovir; lamivudine; saquinavir and valacyclovir.

Preferably, it is not administered in combination with a nephrotoxic antimicrobial agent selected from the group consisting of beta-lactams, polymyxins, aminoglycosides, glycopeptides, sulphonamides, nitroimidazoles, and polyenes. More preferably, cilastatin is not administered in combination with a nephrotoxic antimicrobial agent, such as a nephrotoxic antibiotic.

The term "nephrotoxic antimicrobial agent" as used herein refers to drugs, chemicals, or other substances that either kill or slow down the growth of microbes, which have nephrotoxicity as a side effect. Among the antimicrobial agents there are antibacterial drugs (e.g., vancomycin, gentamicin, polymyxin E), antiviral agents (e.g., foscavir, adefovir, and tenofovir as well as the bisphosphonate pamidronate), antifungal agents (e.g., amphotericin B), and antiparasitic drugs (e.g., sulfadiazine).

In a further particular embodiment, cilastatin is administered in combination with an antimicrobial agent, preferably with an antimicrobial agent other than imipenem, more preferably wherein said antimicrobial agent is not a nephrotoxic antimicrobial agent.

In an additional further particular embodiment, cilastatin is administered in combination with a nephrotoxic antimicrobial agent, more preferably a nephrotoxic antimicrobial agent other than imipenem.

Cilastatin and said other drug, preferably another drug other than imipenem, can be administered in the same or separate pharmaceutical compositions, and at the same time (simultaneously) or at different times (cilastatin is administered before or after said other drug). Further details on the administration schedules of a combination therapy are provided above.

In a particular embodiment, administration of cilastatin is simultaneous to the administration of said other drug, as part of the same or separate compositions. In another particular embodiment, administration of cilastatin is sequential (prior to or subsequent) to the administration of said other drug.

It is contemplated that any embodiment discussed in this specification can be implemented with respect to any medical use, pharmaceutical composition, method of treatment, method of manufacturing a medicament and combination therapies of the invention, and vice versa. It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" may mean "one," but it is also consistent with the meaning of "one or more," "at least one," and "one or more than one". The use of the term "another" may also refer to one or more. The use of the term "or" in the claims is used to mean "and/or" unless explicitly indicated to refer to alternatives only or the alternatives are mutually exclusive.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps. The term "comprises" also encompasses and expressly discloses the terms "consists of" and "consists essentially of". As used herein, the phrase "consisting essentially of" limits the scope of a claim to the specified materials or steps and those that do not materially affect the basic and novel characteristic(s) of the claimed invention. As used herein, the phrase "consisting of" excludes any element, step, or ingredient not specified in the claim except for, e.g., impurities ordinarily associated with the element or limitation.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AB, BBC, AAABCCCC, CBBAAA, CABABB, and so forth. The skilled artisan will understand that typically there is no limit on the number of items or terms in any combination, unless otherwise apparent from the context.

As used herein, words of approximation such as, without limitation, "about", "around", "approximately" refers to a condition that when so modified is understood to not necessarily be absolute or perfect but would be considered close enough to those of ordinary skill in the art to warrant designating the condition as being present. The extent to which the description may vary will depend on how great a change can be instituted and still have one of ordinary skilled in the art recognize the modified feature as still having the required characteristics and capabilities of the unmodified feature. In general, but subject to the preceding discussion, a numerical value herein that is modified by a word of approximation such as "about" may vary from the stated value by ±1, 2, 3, 4, 5, 6, 7, 8, 9, 10, 11, 12, 13, 14 or 15%. Preferably the term "about" means exactly the indicated value (±0%).

The following examples serve to illustrate the present invention and should not be construed as limiting the scope thereof.

EXAMPLES

Example 1.—Material and Methods

Drugs

Crystalline cilastatin was provided by ACS Dobfar (Milan, Italy) and was dissolved in normal 0.9% saline (vehicle).

Animals

Studies were performed on 8-9 week-old male Sprague-Dawley rats weighing 320-370 g (Charles River Laboratories, MA, USA). The animals were housed under controlled light (12-h light-dark cycle), temperature, and humidity with free access to food and water ad libitum, and pre-conditioned in metabolic cages on alternate days for one week. The study was approved by the Institutional Board for Animal Experiments. Animals were handled at all times according to the applicable legal regulations in Royal Decree 53/2013 and Directive 2010/63/UE on the protection of animals used for experimentation and other scientific purposes, under the direct supervision of the veterinary surgeon in charge.

Induction of Sepsis: Cecal Ligation Puncture Model

Sepsis was developed by cecal ligation puncture model (CLP) as described in several papers (Li G et al, Clin Exp Pharmacol Physiol. 2014; 41(7):459-68, Seija M et al, Shock. 2012; 38(4):403-10). Animals were anesthetized with ketamine (Ketolar 50 mg/ml) 90 mg/kg intraperitoneal (ip) and diazepam (Valium 10 mg/2 mL) 5 mg/kg ip. Under sterile conditions a 3-cm midline laparotomy was performed to allow exposure of the cecum, and a 4-0 silk ligature was placed 0.75 cm from the cecal tip. It was punctured once with a 14-gauge needle. A second ligature was placed 1.5 cm proximal to the first one and distal to the ileocecal valve to avoid intestinal obstruction. Three punctures were made in the cecum between the two ligatures with a 16-gauge needle. The cecum was gently squeezed until a 1-mm column of fecal material was exteriorized. The bowel was then returned to the abdomen and the incision was closed in layers. A sham operation (laparotomy and cecal exposure without any other manipulation) was performed as control. At the end of the operation, all rats were resuscitated with normal saline (50 ml/kg body weight) subcutaneously in a single dose and analgesic treatment with buprenorphine (buprex 0.3 mg/ml) 0.1 mg/kg every 12 hours immediately after surgery and until the day of killing.

The rat model of CLP-induced sepsis was chosen because it mimics many pathological features and the clinical course of the disease in humans. CLP-induced sepsis causes increased serum creatinine, BUN and decreased glomerular filtration rate (Cadirci E et al, Clin Exp Immunol. 2011; 166(3):374-84, Li P et at, Critical Care (2015) 19:200) and therefore it has been widely used to investigate novel pharmacological approaches for the prevention and treatment of damaging effects of sepsis (Hubbard W J et al, Shock 2005; 24 (Suppl. 1): 52-7, Doi K et al, J. Clin. Invest. 2009; 119: 2868-78).

Renal Function Monitoring

Serum creatinine, blood urea nitrogen levels (BUN), proteins and other parameters were measured using the Dimension RxL autoanalyzer (Dade-Behring, Siemens, Eschborn, Germany). The glomerular filtration rate was calculated using the creatinine clearance rate.

Renal Histopathological Studies

For light microscopy, paraffin-embedded renal sections (4-mm thick) were stained with hematoxylin-eosin (Sigma-Aldrich, St Louis, Mo.). The kidney injury score was calculated using a previously described semi-quantitative index (Humanes B et al, Kidney International. 2012; 82(6):652-663) as follows: 0, no changes; 1, focal changes that involve 25% of the sample; 2, changes affecting >25 to 50%; 3, changes involving >50 to 75%; 4, lesions affecting >75%. The injury score was calculated by the sum of this semi-quantitative assessment of glomerular damage (mesangial cell proliferation and matrix expansion), tubulointerstitial injury (tubular dilation and/or atrophy), interstitial fibrosis, and inflammatory cell infiltrate. Two independent pathologists scored the kidney injury in a blinded fashion.

Immunohistochemistry

Immunohistochemistry was carried out as described previously (Humanes B et al, Kidney International. 2012; 82(6):652-663). The primary antibodies used were polyclonal goat anti-rat TIM-1/KIM-1/HAVCR (1:20; R&D systems); anti-cleaved caspase-3 (Asp175) (1:50; Cell Signaling Technology, Inc., Beverly, Mass.) mouse monoclonal anti-4-HNE (1:75; Oxis International Inc., Foster City, Calif.); polyclonal rabbit anti-Cu/Zn SOD (1:1000; Assay Designs, Stressgen, Ann Arbor, Mich., USA); monoclonal mouse anti-CD68 (monocyte/macrophage, 1:125, Abd Serotec, Oxford, UK); polyclonal goat anti-VCAM-1 (1:100; Santa Cruz Biotechology, Inc., Beverly, Mass., USA); polyclonal rabbit anti-TGFβ1 antibody (1:100; Santa Cruz Biotechology); monoclonal mouse anti-ICAM-1 (1:100; Santa Cruz). The specificity of the antibodies was verified by controls lacking the primary antibody, producing no background. The surface area labeled by antibodies was evaluated by quantitative image analysis as previously described (Lazaro A. et al. Antiox Redox Signal. 2005; 7:1285-1293). In brief, the percentage of the stained area was calculated as the ratio of suitable binary thresholded image and the total field area. For each sample, the mean staining area was obtained by analysis of the entire sample.

Western Blotting Analysis

Western blotting was performed as described previously (Humanes B et al, Kidney International. 2012; 82(6):652-663). Primary antibodies were as follows: goat anti-kidney injury molecule-1 (KIM-1) polyclonal antibody (R&D Systems, Minneapolis, Minn., USA; dilution 1:2000), rabbit anti-cleaved caspase-3 polyclonal antibody (Asp175) (Cell Signaling Technology, Inc., Beverly, Mass., dilution 1:1000); mouse anti-FasL monoclonal antibody (Santa Cruz Biotechnology, Inc., Beverly, Mass., USA, dilution 1:200), rabbit anti-rodent cleaved caspase-8 (Asp387) (Cell Signaling Technology, dilution 1:1000); rabbit anti-Cu/Zn SOD polyclonal antibody (Assay Designs, Stressgen, Ann Arbor, Mich., USA, dilution 1: 2500). As an internal standard, membranes were re-probed with a mouse monoclonal anti β-actin (Sigma) to verify the equal loading of protein in each line. All signals were visualized with an Alliance 4.7 (Uvitec, Cambridge, UK) and analyzed by densitometric scanning (ImageJ; http://rsbweb.nih.gov/ij/index.html). Results were expressed in arbitrary units (a.u.).

In Situ Detection of Apoptosis

DNA fragmentation as an index of apoptosis was detected by terminal deoxynucleotidyl transferase-mediated dUTP nick end labeling in paraffin-embedded kidney tissue sections using a Fluorescein FragEL DNA Fragmentation Detection Kit (Calbiochem, San Diego, Calif.) following the manufacturer's protocol. The TUNEL-positive cells were visualized with a Leica-SP2 confocal microscope (Leica Microsystems, Heidelberg, Germany). For each renal section, cells undergoing apoptosis were quantified in a blinded fashion by counting all positive apoptotic cells in 30 non-overlapping random fields viewed at 20× magnification.

Urine Levels of Antioxidant Capacity

Urine levels of antioxidant capacity were measured using the commercially available Antioxidant Assay Kit (Cayman Chemical, Ann Arbor, Mich.) according to the manufacturer's protocol (https://www.caymanchem.com/product/709001). The overall antioxidant capacity may give more relevant biological information compared to that obtained by the measurement of individual components, as it considers the cumulative effect of all antioxidants present in plasma and body fluids. The Cayman Chemical Antioxidant Assay Kit measures the total antioxidant capacity of a biological sample. The assay relies on the ability of antioxidants in the sample to inhibit the oxidation of ABTS® (2,2'-azino-di-[3-ethylbenzthiazoline sulphonate]) to ABTS®+ by metmyoglobin (Miller, N.J., Rice-Evans, C., Davies, M. J., et al., Clinical Science 1993, 84, 407-412; Miller, N.J., and Rice-Evans, C. Free Radical Research 1997, 26, 195-199). The capacity of the antioxidants in the sample to prevent ABTS oxidation is compared with that of Trolox, a water-soluble tocopherol analogue, and is quantified as molar Trolox equivalents.

Sirius Red Staining

Collagen fibers were measured as an index of fibrosis by staining with Sirius Red (Sigma-Aldrich) as previously described (Lazaro A. et al. Biomed Res Int. 2016; 2016: 2518626.) The staining score was calculated blind using the following semi-quantitative scale: 0, none; 1, staining between 0 and 25%; 2, staining between 25 and 50%; 3, staining between 50 and 75%; 4, staining >75%.

Statistical Analysis

Quantitative variables were summarized as the mean±s.e.m. Equality of variances was tested with Levene's text. Normally distributed continuous variables with equal variances were analyzed with analysis of variance. If variances were not equal, the Kruskal-Wallis test was performed. Differences were considered statistically significant for bilateral α-values <0.05. Tests were performed using SPSS 11.5 software package (SPSS, Chicago, Ill.).

Example 2.—Effect of Cilastatin on Sepsis-Associated Renal Injury

Experimental Design

The animals were randomly allocated into four groups (n=10 in each group):
i. sham-operated group,
ii. CLP group,
iii. sham-operated group+cilastatin, and
iv. CLP group+cilastatin.

In the treatment groups, the rats were treated with cilastatin 150 mg/kg ip immediately and at 24 h after induction of sepsis or the sham-operation. Cilastatin was substituted by vehicle (0.5 mL/100 g) in the non-treatment groups. The dose of cilastatin was selected based on previous experience (Humanes B et al, Kidney International. 2012; 82(6):652-663, Moreno-Gordaliza E et al, Analytical Chemistry. 2011; 83(20):7933-7940) which showed that cilastatin reduced cisplatin-induced nephrotoxicity. All animals were then placed in the metabolic cages for 24-h urine collection.

Forty-eight (48) hours after the sepsis-induction/sham-operation, all rats were anesthetized with ketamine (10 mg/kg) and diazepam (4 mg/kg) and killed. Blood samples were collected by insertion of a cannula into the abdominal aorta, and serum was isolated by centrifugation in ACUETTE® Z Serum Sep Clot Activator tubes (Greiner bio-one), at 2000 rpm for 15 h at 4° C., and then stored at −80° C. until use. The kidneys were perfused with cold saline and quickly removed. Kidney samples were snap-frozen in liquid nitrogen and kept at −80° C. or fixed in 4% paraformaldehyde (24 h) and paraffin-embedded for the different studies.

Results

Effects of Sepsis and Cilastatin in Classic Renal Function Markers

Figure 1:
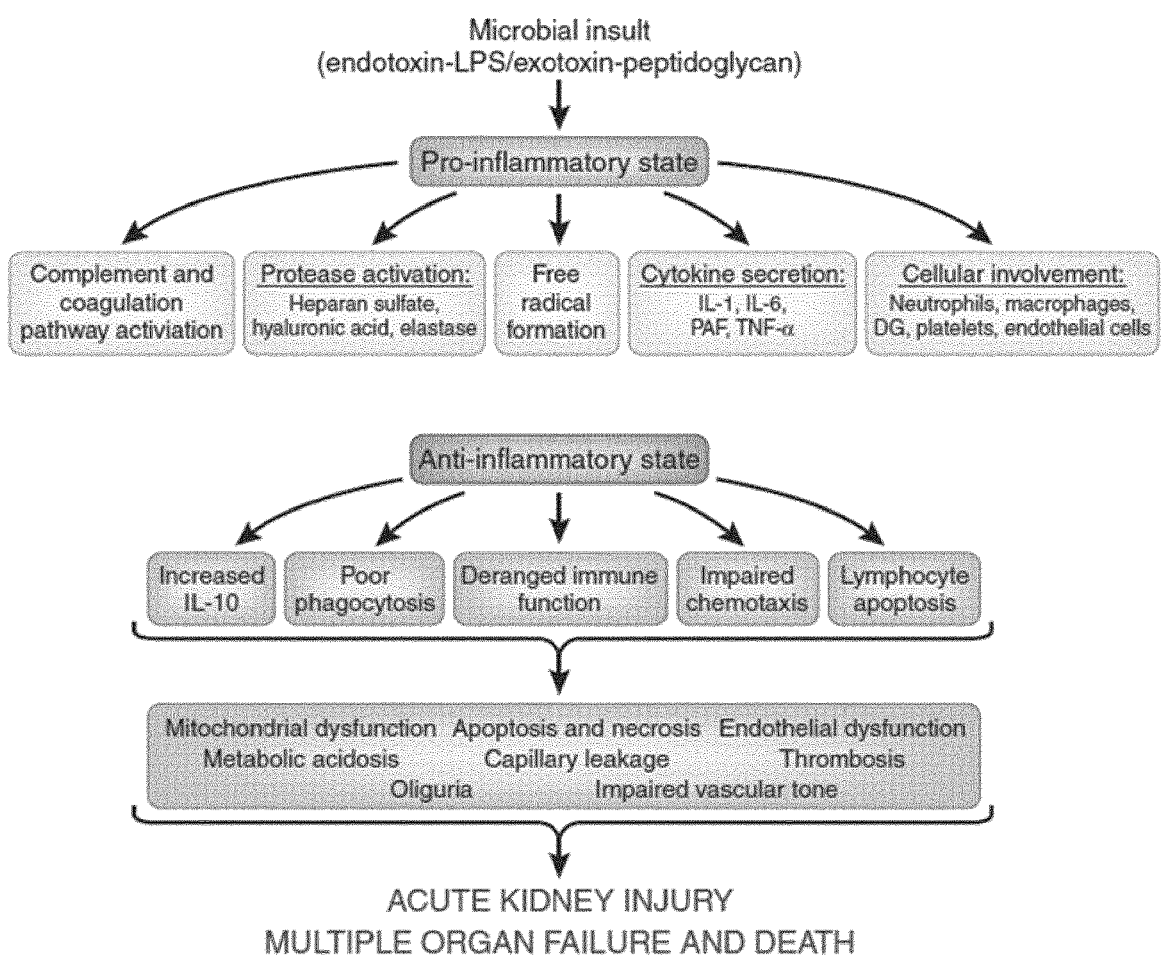
FIG. 1. Key pathogenic pathways involved in the clinical course of sepsis that also have implications in the pathophysiology of septic AKI. From Zarjou et al., 2011, J Am Soc Nephrol 22: 999-1006.
Figure 2:
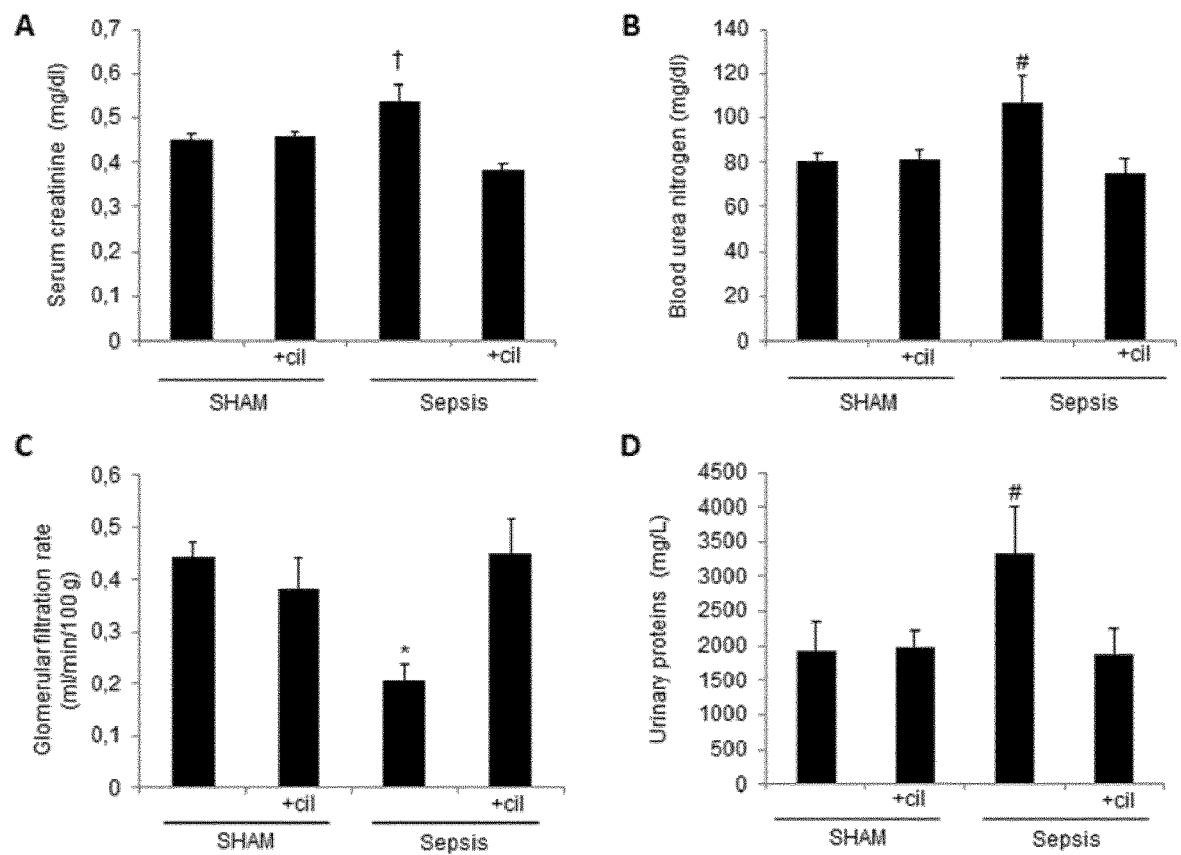
FIG. 2. Effect of cilastatin on sepsis-induced nephrotoxicity in rats. Parameters of renal function at 48 hours after induction of sepsis. (A) Serum creatinine (SHAM: 0.45±0.01; SHAM+cil: 0.46±0.01; sepsis: 0.54±0.04; sepsis+cil: 0.38±0.02), (B) blood urea nitrogen (SHAM: 81±3; SHAM+cil: 81±4; sepsis: 106±12; sepsis+cil: 75±7), (C) glomerular filtration rate (SHAM: 0.44±0.03; SHAM+cil: 0.38±0.06; sepsis: 0.21±0.03; sepsis+cil: 0.45±0.07), (D) proteinuria (SHAM: 1920±420; 1983±226; 3316±682; 1889±347). Sepsis increases serum creatinine, blood urea nitrogen and protein excretion in the urine, and reduces glomerular filtration rate in comparison with sham groups. Cilastatin significantly improved all the parameters. Results are expressed as mean±s.e.m.; n=8-10 animals per group. †p≤0.025, *p<0.035, # p<0.05 vs all groups. Cil=Cilastatin.

Sepsis increased serum BUN and creatinine levels, and decreased the glomerular filtration rate in comparison with the sham group (FIG. 2). However, these dysfunctions were totally prevented in the septic animals by cilastatin. Protein excretion also increased in the CLP group but was significantly reduced by cilastatin (FIG. 2D). Cilastatin alone had no effect on these parameters compared with the sham group.

Effects of Sepsis and Cilastatin in Acute Kidney Injury Biomarker KIM-1

The renal effect of sepsis was confirmed by the increase of the acute kidney injury biomarker KIM-1 at protein level as determined by immunohistochemistry (FIGS. 3 A-E) and Western blot (FIGS. 3 F-G). Cilastatin (sepsis+cil) partially restored the protein into control (SHAM) levels. As shown in FIGS. 3E & 3G reduction of KIM-1 protein levels was statistically significant with respect to the group of septic animals with no treatment. On the other hand, cilastatin alone (SHAM+cil) had no effects on renal KIM-1.

Cilastatin Ameliorated Histopathological Sepsis-Associated Renal Injury

The kidneys from the sham group showed normal glomeruli and tubules histology (FIGS. 4A and 4E). In contrast, the kidneys of the sepsis group revealed structural damage characterized by mild leukocyte infiltration, swelling of the tubular cells, congestion in the interstitium and brush border loss and hyaline casts in renal tubules (FIG. 4C). Moreover, capillary congestion and glomerular tuft collapse were observed in the kidneys of the sepsis animals with enlargement of Bowman's capsule (FIGS. 4C and 4G). Compared with the sham group, cilastatin alone had no effect on renal morphology (FIGS. 4B and 4F) but its use in the sepsis groups was found to reduce many of the symptoms of renal damage (FIGS. 4D and 4H). The semi-quantitative histological injury score was significantly higher in sepsis-induced rats than in controls. Cilastatin alone has no effect on renal morphology of the sham group but reduced the renal injury score in sepsis-induced rats. (FIG. 4I).

Cilastatin Reduces Sepsis-Induced Apoptosis

Figure 5:
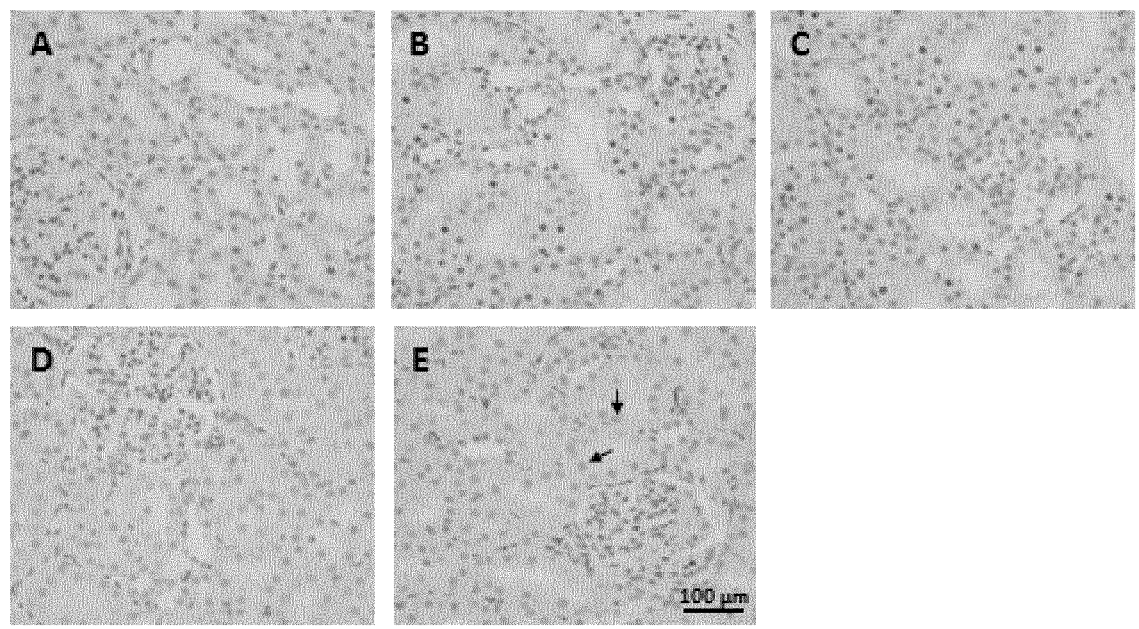
FIG. 5. Effect of cilastatin on sepsis-induced caspase-3 expression. Localization of active cleaved caspase-3 in kidney sections. A) sham; B and C) sepsis group; D) sham+cilastatin; and E) sepsis+cilastatin. Note that the cellular nuclei in the renal tubules are the main site of caspase-3 activation in sepsis-animals (magnification, ×20). Cilastatin significantly reduced expression of active caspase-3 induced by sepsis (arrows). Bar, 100 μm F) Semiquantification of cleaved caspase-3 immunostaining in kidney samples. G) Representative Western blot of cleaved caspase-3 in renal cortex. H) Densitometric analysis of Western blots of active cleaved caspase-3. Data are expressed as mean±s.e.m., n=8-10 animals per group. *P≤0.005 vs. all other groups. Cil, cilastatin; a.u., arbitrary units.
Figure 5:
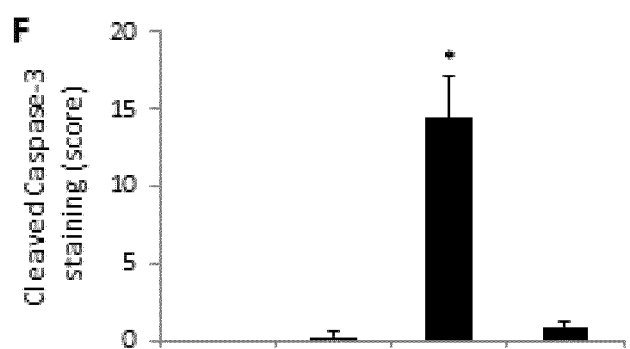
Figure 5:
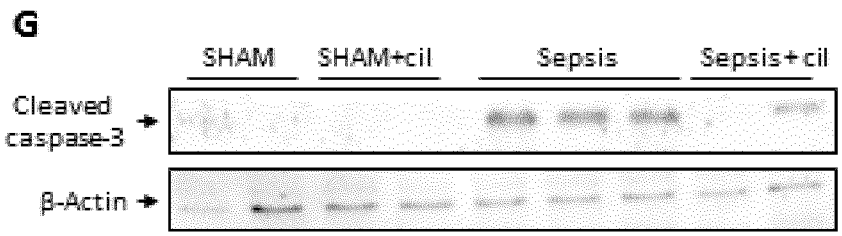
Figure 5:
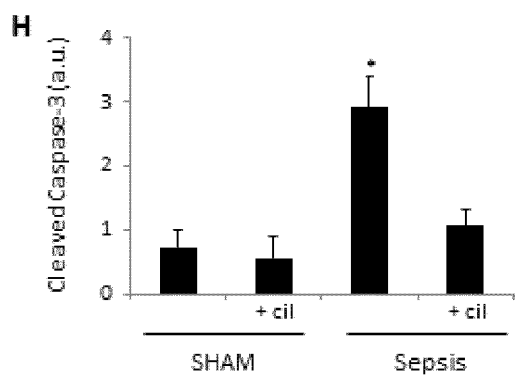
Figure 6:
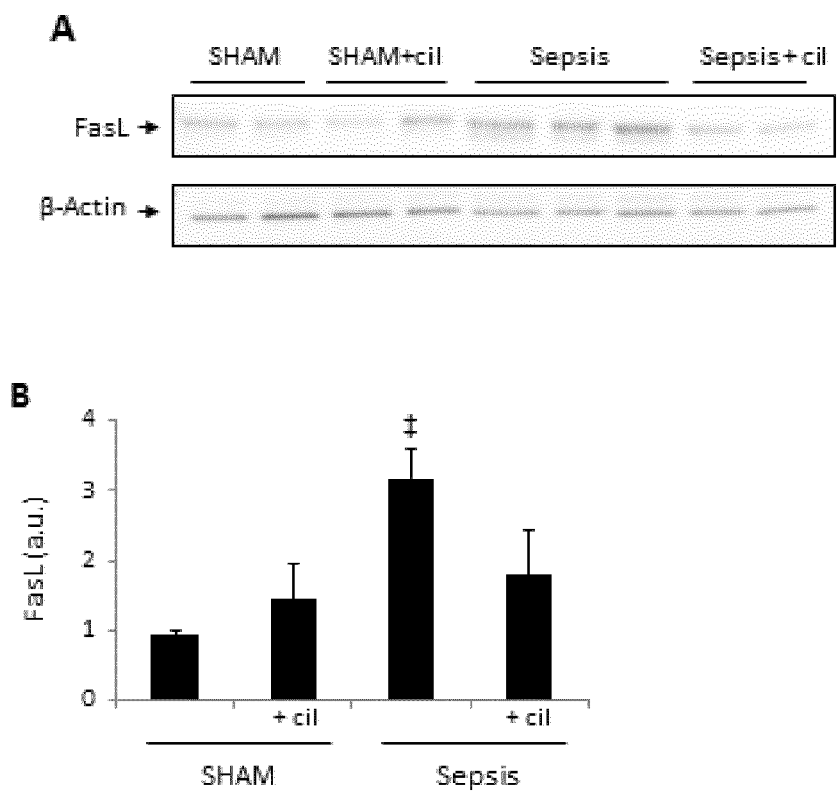
FIG. 6. Effect of cilastatin on sepsis-induced caspase-8 expression. A) Representative Western blot of FasL in renal cortex of the different groups. B) Densitometric analysis of Western blots of FasL. C) Representative Western blot of cleaved caspase-8 in renal cortex of the different groups. B) Densitometric analysis of Western blots of active cleaved caspase-8.
Figure 6:
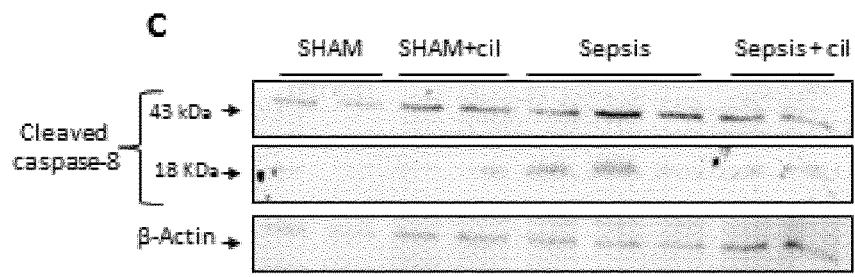
Figure 6:
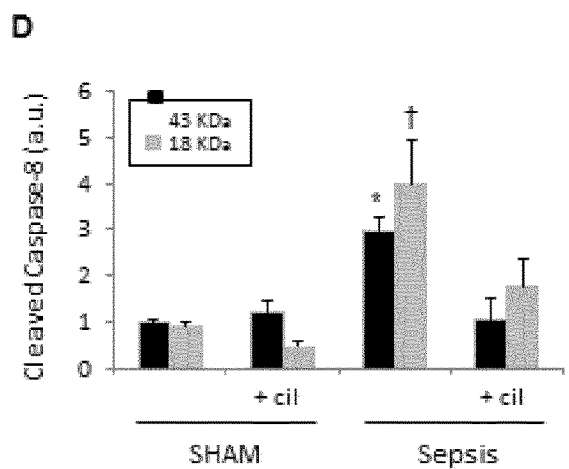

Expression of Molecules Levels in Mitochondrial and Extrinsic Pathway of Apoptosis Renal sections from the sepsis group displayed increased activated cleaved caspase-3 staining in renal tubules compared to untreated kidneys and kidneys treated with cilastatin only (FIG. 5). Cilastatin significantly lowered the elevated caspase-3 levels, as assessed both by immunohistochemistry (FIGS. 5 E and 5F) and by Western blot of the renal cortex (FIGS. 5G and 5H). On the other hand, renal cortex FasL and cleaved caspase-8 were also markedly increased as a result of sepsis; both were also attenuated by cilastatin treatment (FIG. 6).

In Situ Detection of Apoptosis

Apoptosis in the kidney was assessed using the terminal deoxynucleotidyl transferase (TdT)-mediated dUTP nick end-labeling (TUNEL) assay. Sepsis increased the number of apoptotic nuclei compared with the control and control plus cilastatin groups (FIG. 7A). Cilastatin significantly decreased the number of TUNEL-positive cells (FIGS. 7A and 7B).

Effect of Cilastatin on Sepsis-Induced Oxidative Stress

Cilastatin Enhances Antioxidant Defences

To evaluate the role of cilastatin in countering sepsis-induced oxidative stress, we measured antioxidant capacity in urine. Urine from septic rats showed a decrease in the antioxidant capacity compared to control group, and this was improved by cilastatin (FIG. 8G). One of the enzymes involved in this antioxidant defense is the Cu/Zn SOD. Cu/Zn SOD expression was decreased in renal cortex of septic rats, while cilastatin was able to restore its expression, as shown by immunohistochemistry and Western blotting (FIG. 8A-F).

Cilastatin Reduces Lipid Peroxidation 4-hydroxy-2-nonenal (4-HNE) is a product of fatty acid oxidation. Sepsis enhanced 4-HNE staining in the kidneys when compared with the controls (FIG. 9A-C). This was completely prevented by cilastatin (FIGS. 9D and 9E). Cilastatin alone did not modify this variable compared with the control group.

Effect of Cilastatin on Sepsis-Induced Inflammation

Cilastatin Ameliorates Renal Inflammatory Cell Infiltration

In the immunohistochemical studies, greater recruitment of monocytes/macrophages (as evidenced by labeling with CD68) was seen in the renal samples of septic rats than in controls (FIG. 10A-C). Cilastatin-treated rats had fewer CD68 positive cells compared to the sepsis group (FIGS. 10D and E).

The adhesion molecules are of great importance in the mediation of adhesion of leukocytes to vascular endothelium. FIG. 10 shows the renal staining of VCAM-1 and ICAM-1 by immunohistochemistry. Sepsis increased the expression of both ICAM-1 and VCAM-1 compared with the control groups. Treatment with cilastatin significantly reduced sepsis-induced changes. Cilastatin alone had no effects on ICAM-1 and VCAM-1 presence on kidney tissue (FIG. 11).

Cilastatin Reduces Increased Expression of TGFβ

TGFβ is a profibrotic cytokine that contributes to worsening of kidney damage. By immunohistochemistry, higher levels of TGFβ were observed in renal tissue of septic rats than in control groups. Cilastatin treatment significantly decreased TGFβ1 levels in septic animals (FIGS. 12A and 12B).

On the other hand, we analyzed the appearance of fibrosis in the same animals by Sirius red staining, and its correlation with TGFβ levels. As can be seen in FIGS. 12A and 12C, although there was trend for higher fibrosis expression in septic animals, it did not reach statistical significance. This may be explained by the fact that the animals were sacrificed at 48 hours after surgery, but it is observed that the profibrotic mechanisms have already begun.

Example 3.—Effect of Cilastatin on CLP-Induced Sepsis Mortality

Experimental Design

Another experimental model was performed in order to determinate the mortality of septic process at 48 h and survival obtained after cilastatin treatment. The induction of sepsis was the same as described above with the difference that the three punctures in the cecum between the two ligatures were made with a 14-gauge needle and the other puncture (in the cecal tip) was made with a 16-gauge needle. This led to a more aggressive model of sepsis.

A total of 12 animals were used, which were randomized into 2 groups with a sample size n=6 animals per group. The study groups and their treatments were therefore as follows:

CLP (sepsis) group: animals with induction of aggressive sepsis by CLP surgery plus vehicle of cilastatin in the same manner and volume as in group CLP+cilastatin.

CLP+cilastatin group: animals with induction of aggressive sepsis by CLP plus cilastatin (dissolved in saline serum) at a dose of 150 mg/kg/body weight immediately and a t 24 h after induction of sepsis.

At 48 hours after induction of sepsis, surviving animals in both groups were quantified.

Results

Mortality in sepsis is a very common fact. In an aggressive model of sepsis 5 of 6 animals died before reaching 48 h after CLP surgery. Treatment with cilastatin decreased the mortality by 33% (FIG. 13).

The invention claimed is:

1. A method for treating sepsis in a mammalian subject in need thereof, comprising administering a therapeutically effective amount of cilastatin and an antimicrobial drug to the subject, with the proviso that said antimicrobial drug is not a beta-lactam nephrotoxic antimicrobial agent.

2. A method for treating sepsis-associated acute kidney injury (SA-AKI) in a mammalian subject in need thereof, comprising administering a therapeutically effective amount of cilastatin to the subject.

3. A method for preventing sepsis-associated acute kidney injury (SA-AKI) in a mammalian subject having sepsis, comprising administering a therapeutically effective amount of cilastatin and optionally another drug to the subject, with the proviso that said other drug is not a beta-lactam nephrotoxic antimicrobial agent.

4. The method of claim 1, wherein said subject suffers from severe sepsis, or septic shock, or both.

5. The method of claim 1, wherein said subject is a human subject.

6. The method of claim 1, wherein cilastatin is administered by the oral, sublingual, transdermal or parenteral route.

7. The method of claim 1, wherein cilastatin is administered by the parenteral route at a dosage of 10 to 50 mg/kg of body weight.

8. The method of claim 1, with the further proviso that said antimicrobial drug is additionally not a nephrotoxic antimicrobial drug selected from the group consisting of gentamicin; kanamycin; tobramycin; amikacin; netilmycin; bacitracin; neomycin; metronidazole; polymyxin B; polymyxin E (colistin), trimethoprim; sulfisoxazole; sulfamethoxazole; methenamine; vancomycin; spectinomycin; chloramphenicol; amphotericin B, pentamidine, pentamidine isoethionate; atavaquone; rifampin; paraaminosalicylic acid; isoniazid; capreomycin; acyclovir; AZT; 3TC; vidarabine; cidofovir; lamivudine; saquinavir and valacyclovir.

9. The method of claim 1, wherein said antimicrobial drug is not a nephrotoxic antimicrobial drug.

10. The method of claim 1, wherein cilastatin and said antimicrobial drug are part of the same pharmaceutical composition.

11. The method of claim 1, wherein cilastatin and said antimicrobial drug are part of different pharmaceutical compositions that can be administered at the same time or at different times; with the proviso that, when administered at different times, the pharmaceutical compositions are administered sufficiently close in time to provide for a potentiating or synergistic response to occur.

12. The method of claim 3, wherein cilastatin is administered as a single agent.

13. The method of claim 6, wherein cilastatin is administered by the intramuscular, intraperitoneal or intravascular route.

14. The method of claim 6, wherein cilastatin is administered by the intravenous route.

15. The method of claim 7, wherein cilastatin is administered by the parenteral route at a dosage of 22 to 26 mg/kg of body weight for a human adult.

16. The method of claim 7, wherein cilastatin is administered by the parenteral route at a dosage of 34 to 38 mg/kg of body weight for a human child.

17. The method of claim 1, wherein cilastatin and said antimicrobial drug are administered within seconds or minutes to within about 1 or 3 hours from each other.

18. The method of claim 3, wherein cilastatin and said other drug are administered within seconds or minutes to within about 1 or 3 hours from each other.

19. The method of claim 3, with the further proviso that said other drug is additionally not a nephrotoxic antimicrobial drug selected from the group consisting of gentamicin; kanamycin; tobramycin; amikacin; netilmycin; bacitracin; neomycin; metronidazole; polymyxin B; polymyxin E (colistin), trimethoprim; sulfisoxazole; sulfamethoxazole; methenamine; vancomycin; spectinomycin; chloramphenicol; amphotericin B, pentamidine, pentamidine isoethionate; atavaquone; rifampin; paraaminosalicylic acid; isoniazid; capreomycin; acyclovir; AZT; 3TC; vidarabine; cidofovir; lamivudine; saquinavir and valacyclovir.

20. The method of claim 3, wherein said other drug is not a nephrotoxic antimicrobial drug.

21. The method of claim 3, wherein the cilastatin and said other drug are part of the same pharmaceutical composition.

22. The method of claim 3, wherein the cilastatin and said other drug are part of different pharmaceutical compositions that can be administered at the same time or at different times; with the proviso that, when administered at different times, the pharmaceutical compositions are administered sufficiently close in time to provide for a potentiating or synergistic response to occur.

23. A method for reducing mortality in a mammalian subject having sepsis or SA-AKI, comprising administering a therapeutically effective amount of cilastatin and optionally another drug to the subject, with the proviso that said other drug is not a nephrotoxic beta-lactam antibiotic.

* * * * *